United States Patent [19]

Tamari

[11] Patent Number: 5,215,450
[45] Date of Patent: Jun. 1, 1993

[54] INNOVATIVE PUMPING SYSTEM FOR PERISTALTIC PUMPS

[76] Inventor: Yehuda Tamari, 21 Singworth St., Oyster Bay, N.Y. 11771

[21] Appl. No.: 669,641

[22] Filed: Mar. 14, 1991

[51] Int. Cl.$^5$ .................. F04B 43/08; F16L 11/06
[52] U.S. Cl. .................. 417/474; 417/477; 417/478; 138/119
[58] Field of Search .............. 417/474–478; 138/119

[56] References Cited

U.S. PATENT DOCUMENTS

| | | | |
|---|---|---|---|
| 1,653,933 | 2/1913 | Stowe | 138/119 |
| 3,508,587 | 4/1970 | Mauch | 138/119 |
| 3,720,235 | 3/1973 | Schrock | 138/119 |
| 3,721,269 | 3/1973 | Choate | 138/119 |
| 3,942,915 | 3/1976 | Thomas | 417/477 |
| 4,131,399 | 12/1978 | Calvet | 417/477 |
| 4,257,422 | 3/1981 | Duncan | 138/119 |
| 4,346,705 | 8/1982 | Pekkarinen | 604/30 |
| 4,417,856 | 11/1983 | Minissian | 417/477 |
| 4,421,506 | 12/1983 | Danby | 417/474 |
| 4,465,721 | 8/1984 | McAlister | 528/86 |
| 4,496,295 | 1/1985 | King | 417/477 |
| 4,515,589 | 5/1985 | Austin et al. | 604/122 |
| 4,650,471 | 3/1987 | Tamari | 417/477 |
| 4,671,792 | 6/1987 | Bonsanyi | 417/474 |
| 4,702,675 | 10/1987 | Aldrovandi | 417/477 |
| 4,767,289 | 8/1988 | Parrott | 417/477 |
| 4,909,713 | 3/1990 | Finsterwald | 417/477 |
| 4,976,593 | 12/1990 | Miyamoto | 417/476 |

FOREIGN PATENT DOCUMENTS

| | | | |
|---|---|---|---|
| 395239 | 7/1933 | United Kingdom | 138/119 |
| 2179404 | 3/1987 | United Kingdom | 417/477 |

OTHER PUBLICATIONS

Cole–Parmer Instrument Company Catalog, Tubing pp. 558–561.

Primary Examiner—Richard A. Bertsch
Assistant Examiner—Peter Korytnyk

[57] ABSTRACT

The invention is a pumping system composed of a relatively thin wall extruded tubing that in different forms can provide flow regulation for peristaltic pumps, reduce spallation, extend pumping life, provide means to measure inlet and outlet pressure of the peristaltic pump and limits the inlet and outlet pressure generated by peristaltic pumps, and a special peristaltic pump that takes advantage of the characteristics of the aforementioned tubing. The invention has particular usefulness in the medical industry for pumping physiological or nutritional liquids.

25 Claims, 6 Drawing Sheets

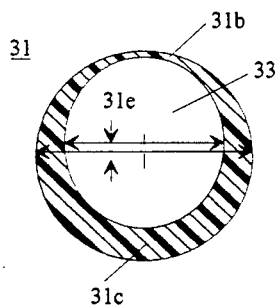
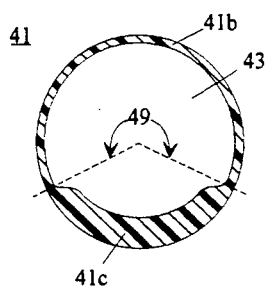
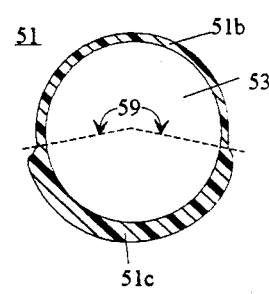
Fig. 3(a)  Fig. 4(a)  Fig. 5(a)
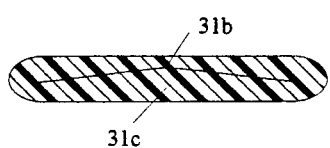
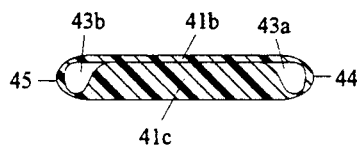
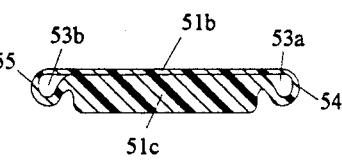
Fig. 3(b)  Fig. 4(b)  Fig. 5(b)
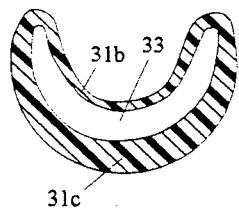
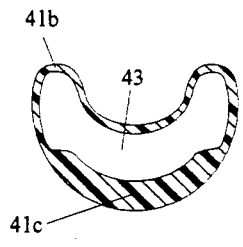
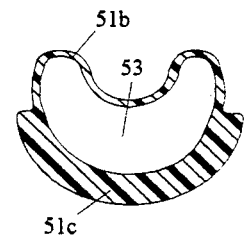
Fig. 3(c)  Fig. 4(c)  Fig. 5(c)
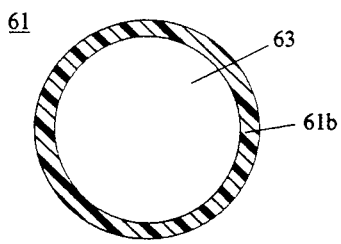
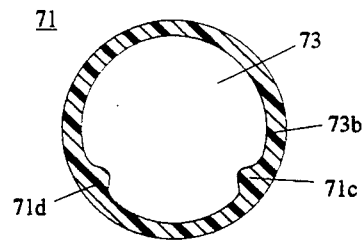
Fig. 6(a)  Fig. 7(a)
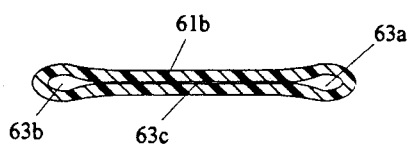
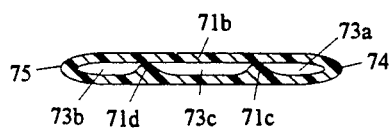
Fig. 6(b)  Fig. 7(b)

INNOVATIVE PUMPING SYSTEM FOR PERISTALTIC PUMPS

CROSS-REFERENCE TO RELATED APPLICATIONS

This application is related to co-pending co-application U.S. Ser. No. 07/410,845 now abandoned filed Sep. 22, 1989 entitled "Pressure Sensitive Valves for the Extracorporeal Circuit" containing similar pressure isolators for similar applications, the disclosure of said application being incorporated herein by reference thereto.

BACKGROUND OF THE INVENTION

1. Field of the Invention

The invention discloses a tubing for pumps, said tubing having at least one longitudinal relatively thin wall, that provides means to measure inlet and outlet pressure of pumped fluid, without contacting the fluid, and to regulate flow as a function of inlet outlet pressure of the pump. A peristaltic pump designed to take advantage of the special properties of the thin wall tubing is also disclosed. There are three major applications for the invention: roller pumps used for extracorporeal circulation, peristaltic pumps used for IV infusion, and peristaltic pumps for industry. The description of the invention hereinafter, makes extensive use of extracorporeal applications. This emphasis is made for description only. It should be understood that the described art is easily extended to the other aforementioned applications.

2. Description of the Prior Art.

The simplicity and availability of the standard roller pump have made it the choice for extracorporeal circulation. This pump is widely used in dialysis, routine cardiopulmonary bypass and long term pumping such as extracorporeal membrane oxygenators, (ECMO) and left and/or right heart bypass. The standard tubing used to pump blood with the roller pump is almost always polyvinyl chloride (PVC) with a nominal size from ¼" ID with wall of 1/16" (Dialysis and pediatric cases) to ⅜" or ½" with a 3/32" wall. PVC tends to abrade easily, does not have the sufficient resilience at high pump speed to return to its natural diameter and tends to develop cracks along the edges that are bent repeatedly by the action of the pump. Manufacturers of roller pumps for extracorporeal circulation recommend that thick wall PVC tubing be used to overcome some of these problems. Use of thick walled tubing results in many disadvantages, among which are the following:

a) The roller pump maintains constant flow independent of clinically expected changes in inlet or outlet pressures. Thus, a decrease in blood supply at the pump inlet, without a concomitant decrease in pump speed, can cause excessive suction leading to air embolism, thrombosis and damage by the "venous" cannula to the patient's intima. Tests conducted by the inventor have shown that when starting at equilibrium using a polyvinyl chloride tube with ⅜" ID and 1/16" wall, a 30% drop in inlet flow caused the inlet pressure to drop from 0 to −250 mmHg; with a 3/32" wall tubing the pressure drop was from 0 to over −500 mmHg. The combination of constant flow and an arterial line that is accidentally clamped or kinked, or an arterial cannula that is positioned against the patient's intima, can generate excessive pressures at the outlet of the pump which at the extreme, can blow up a connector, tube, or an oxygenator.

To overcome these potential dangers, bubble oxygenators have blood level detectors which stop the pump when the blood level drops below a preset level, or a floating ball valve (SG-10 Ball Valve American Omni Medical Inc. Costa Mesa Calif. 92626), that closes when the blood level drops below the oxygenator outlet port. In closed systems such as ECMO or dialysis, easily collapsible bladders have been placed at the inlet to the pump such that at too high a suction, the bladder collapses actuating a microswitch which stops the pump. The pump restarts when the bladder refills. With current thick wall tubing this often results in very intermittent pumping because the slightest change in inlet flow causes the bladder to empty. Roller pumps with a microprocessor control servomotor may overcome some of these problems but their expense limits their use. When the roller pump is used during cardiac surgery for venting the left ventricle or for returning shed blood from the chest cavity it requires either the constant surveillance by a trained perfusionist to assure that excess suction does not occur, or the use of a suction relief valve such as the RLV-2100 "B" (American Omni Medical Inc., Costa Mesa Calif. 92626). This particular valve introduces air into the blood line which can increase hemolysis.

b) The power required to rotate the roller against the elastic force of the tubing wall is significant, requiring very powerful motors and indirect drive (e.g. gears) which, as will be described hereinafter, results in low pumping efficiencies.

c) The pumping rate is limited by the rotational speed of the motor and the resilience of the tubing returning the squeezed tubing wall to its natural open state. As will be described hereinafter, with the present invention of a thin wall tubing, a positive inlet pressure can better serve to maintain the tubing open.

d) At high rotational pump speed, the compression and decompression of the tubing wall generates heat and large flexure stresses that can change wall thickness resulting in a change in occlusiveness and limiting the pumping life of the tubing.

Studies by the inventor with various sized tubing with hardness of 60-75 Shore-A pumped with a roller pump indicate that normalized flow, expressed as a percentage of flow at atmospheric inlet pressure, was dependent on inlet pressure and independent of pump speed. It was also shown that the rate of change in normalized flow as a function of inlet pressure, referred to as flow sensitivity, (% flow)/mmHg, was directly related, and highly correlated ($r^2 > 98\%$) to the ratio of inside diameter (ID) to wall thickness (Wall) as follows:

$$\text{Flow sensitivity} = (1/3100)(ID/Wall)^{3.24}$$

or $$ID/Wall = 12(\text{flow sensitivity})^{0.309}$$

Thus, a small change in ID/wall results in a large change in flow sensitivity.

U.S. Pat. Nos. 4,515,589 and 4,767,289 (manufactured by Sarns/3M Corp. of Ann Arbor Mich. as the "Safety Loop"), and 4,650,471, described devices to be used with the roller pump to regulate flow as a function of inlet pressure. Both of these devices utilize thin wall tubing (e.g. 0.375" ID with a 0.010" wall with ID/Wall = 37.5) housed inside standard thick wall tubing. The thin wall tubing, which collapses easily in response to changes in inlet pressure, provides flow regulation and the thick wall housing provides mechanical support, prevents the thin wall tubing from getting tangled within the raceway of the roller pump and supports the thin walled tubing in the event that the outlet pressure causes the thin wall to herniate. The inventors disclosed the use of polyurethane as a possible material for the thin wall tubing in combination with a thick wall housing. Though excellent flow control can be achieved, the thick wall housing adds to the torque requirements of the pump.

The French Company Rhone-Poulenc sells the RP.01 Blood Pump that utilizes a silicone tube (10 mm ID by with a 1.3 mm wall, resulting in a relatively large ratio of ID to wall thickness of 7.7) that starts to collapse when the inlet pressure to the pump drops below −50 mmHg. As the inlet pressure drops from −50 to −100 mmHg the flow drops fivefold. The RP.01 pump also has a specially shaped roller that occludes only the central section of the tubing. This forms a channel at each edge of the tubing when the tubing is squeezed by the roller. Should air be aspirated by the pump, the low viscosity air would reduce the suction and stop blood flow. This pump tubing has four drawbacks: first, it can only be used with its own specially designed roller pump, second, there is no adjustment of the internal pressure about which the flow is controlled; third, the pump does not generate an outlet pressure much above 250 mmHg; and fourth the tubing used is silicone which easily spallates and has a short pumping life.

Two types of pump tubing made of polyurethane have been available commercially. First, a nominal ⅜" ID (measured 0.365") with a 0.040" wall pump chamber was manufactured by dip molding Biomer, a polyether-polyurethane (Ethicon, a Division of Johnson and Johnson, Sommerville N. J.). Additional mechanical strength was provided to this pump chamber with circumferential wrapping of fiberglass filament in a spiral manner about the wall of the Biomer. This Pump Chamber was limited in use because it was prohibitively expensive, over $100/ea in 1972. Second, a proprietary medical grade polyether-polyurethane (Pellethane 2363-80A) was extruded into standard size tubing (⅜" ID with 1/16" wall) for the roller pump (Tygothane by Norton Co., Akron Ohio 44309). This tubing proved to have longer pumping life and lower spallation (i.e. higher resistance to abrasion) than the standard tubing made of polyvinyl chloride (e.g. Tygon S-50-HL, Norton Co., Akron Ohio). However, Tygothane tubing was significantly harder then the standard polyvinyl chloride tubing (81 Shore A as compared to 65 Shore A) and caused the roller pumps to fail. It therefore never was used extensively and is no longer manufactured for roller pump use.

Theodore Kolobow of NIH reported [Transactions of American Society for Artificial Organs 15:172–177, 1969)] on a large bore thin walled tubing (15.3 mm ID, and 0.886±0.25 mm wall, resulting in an ID/Wall=17.3) fabricated of Biomer by dip molding to give an " . . . exact clearance . . . " for setting the pump occulsion during long term pumping. This tubing was not used for flow control, which was achieved with a collapsible bladder in the venous line. Two years later Kolobow abandoned the thin wall tubing and substituted the aforementioned reinforced Biomer pump chamber made by Ethicon (ID/Wall=9). Currently Dr. Kolobow uses the aforementioned Tygothane tubing (½" ID by 1/16" wall) with a ID/Wall of 8.0. Tests by the inventor with that Tygothane tubing indicate that less than a 5% decrease in inlet flow results in a −400 mmHg decrease in inlet pressure.

Polyurethane was also used as an internal thin liner (about 0.010" thick) for standard polyvinyl chloride tubing (Bev-A-Line III). This tubing was coextruded and was claimed to have a much lower spallation and a negligible migration of plasticizers into blood. Its ID/Wall ratio equaled that of standard tubing and its major disadvantage was that the polyurethane liner separated from the polyvinyl chloride tubing when placed in the roller pump. This tubing is no longer manufactured for roller pump use.

Pierson et. al. [Transactions of American Society for Artificial Internal Organs 8:105–114, 1962] described a ¼" to ½" ID thin walled tubing (0.020" wall, resulting in an ID/Wall as high as=18.7) fabricated of rubber latex to be used as an implantable or extracorporeal portable heart pump in conjunction with a high speed (RPM>500) nonocclusive roller pump. Though this tubing was used for flow control as a function of inlet pressure, it was latex, which is manufactured by dipping, has a short pumping life, spallates, and could not support an outlet pressure higher than 100 mmHg. Such low pressure is incompatible with current extracorporeal technology. The motor used for the roller pump incorporated beveled gears which required more than 3 times the power required to pump blood at 2 l/min and an inlet pressure of 20 mmHg and outlet pressure of 100 mmHg. No reports were found of this system after the above mentioned reference. The inventor's experience with latex tubing suggests that such tubing may have very desirable flow characteristics as a function of inlet pressure but it cannot support clinically relevant outlet pressure [Tamari et.al. Transactions of American Society for Artificial Internal Organs 30:561–566, 1984]. Further, thin wall latex tubing cannot be used in a fully occlusive roller pump because the rollers would tend to stretch the elastic wall along the direction of rotation.

The poor choice of material may be why all the major manufacturers of roller pumps (e.g. Shiley, Cobe, 3M/Sarns) and of perfusion tubing (e.g. Baxter/Bentley, Norton, Shiley, Texas Medical Products) recommend using tubing #2 and #4 in Table 1 which have an ID/Wall ratio of 4.0. Cole-Parmer, a major supplier of peristaltic pumps and tubing for industry, does not have tubing with a ratio larger than 6 with most of the tubing having a ratio of 3 or less. The major reason for using a thick wall is to assure that pump flow does not change due to tubing fatigue resulting in a change from a round to oval shape cross section. This occurs because the tubing has insufficient resilience to withstand the repeated squeezing of the tube wall by the action of the pump. None of the manufacturers recommend using polyurethane tubing. Whenever commercially available thin wall tubing was used with the roller pump it was either mechanically supported (U.S. Pat. Nos. 4,515,589 and 4,767,289), reinforced with fiber filament (Ethicon) or a polyvinyl chloride liner (Bev-A-Line III), manufactured by dipping or could not support an outlet pressure greater than 100 mmHg.

The foregoing prior art may be summarized in table form as illustrated in Table 1 below. Tubing #4 and #5 are the most widely used tubing for roller pumps during adult cardiopulmonary bypass procedures.

TABLE 1

Representative tubing used with peristaltic pumps.

| # | Tubing Usage | ID | Wall | ID/Wall | Material | Hardness Shore A | Strength PSI | Life Hours | Elong % |
|---|---|---|---|---|---|---|---|---|---|
| 1 | CPB | 3/16" | 1/16" | 3.0 | PVC | 60–70 | 2200 | — | 350 |
| 2 | Dial + CPB | ¼" | 1/16" | 4.0 | PVC | " | | — | " |
| 3 | CPB | ⅜" | 1/16" | 6.0 | PVC | " | | 23 | " |
| 4 | CPB | ⅜" | 3/32" | 4.0 | PVC | " | | 55–123 | " |
| 5 | CPB | ⅜" | 3/32" | 4.0 | PVC/PU | " | | 55–123 | " |
| 6 | CPB | ½" | 3/32" | 5.3 | PVC | " | | — | " |
| 7 | RP.01 | 10 mm | 1.3 mm | 7.7 | Silicone | | 1150 | 55 | 360 |
| 8 | Ethicon* | .365" | .041" | 9.0 | Biomer | | | | |
| 9 | Kolobow** | .500" | .030" | 17.3 | Biomer | | | | |
| 10 | Pierson** | ⅜–½" | .020" | 18.7 | Latex | | | | |
| 11 | IV Pumps | .100" | .020" | 5.0 | PVC | 60–75 | | | |
| 12 | Cole Parmer | 1/16" | 1/16" | 1.0 | PVC, Sil, | | | | |
| 13 | Cole Parmer | 5/16" | 1/16" | 5.0 | Neoprene | | | | |
| 14 | Invention | .375" | .030" | 12.5 | PEPU | 72–80 | 4500 | >1700 | 650 |

ID — inside diameter, ID/wall — ID divided by wall thickness. Hardness at room temperature. Strength — tensile strength. Life — pumping life obtained at 150–160 RPM and 500 mmHg outlet pressure at 30° C., Elong % — percent elongation at break. CPB — Cardiopulmonary bypass, Dial — Dialysis. PVC/PU Polyurethane lined PVC tubing, PEPU — Polyether-Polyurethane.
*Reinforced with spiral fiberglass filaments.
**Made by dipping.

Independent of the tubing, damage to blood by the pumping action of the roller pump is mainly due to crushing of the cells between the opposite walls of the tubing. Blood damage is minimized by setting the pump nonocclusively; that is, allowing the space between the roller and the backplate of the pump head to be greater than twice the tubing wall thickness. The nonocclusive setting, typically allowing a 100 cm vertical column of blood to fall 2.5 cm/min, requires a very precise distance between the tubing rollers and the pump head raceway. Nonocclusive settings do not necessarily guarantee that the walls at the midsection of the tube do not contact; the cross section of squeezed tube within the roller head takes the shape of a figure "8" with the bent edges of the tubing last to occlude, and as will be hereinafter described in reference to FIG. 6(b). This is one of the main reasons that hemolysis rate for the roller pumps reported in the literature have been inconsistent. Another reason is that occlusion setting can also be inconsistent due to either nonuniform distance along the circumference of the housing backplate and the roller and variation in the wall thickness of standard perfusion tubing. The latter can initially be due to manufacturing (±0.003" for one wall and ±0.006" for two walls) and, during pumping, due to temperature variations and material flow. The inability of the user to assure consistent low occlusion may be the reason that less occlusive setting causes less blood damage.

Some pump manufacturers (e.g. Cobe Laboratories) designed spring actuated rollers that push on the tubing, overcoming the elasticity of the tubing wall, and provide uniform occlusion independent of the aforementioned distance and wall variations. The disadvantages of this system are that the tubing is set occlusively, increasing blood damage, and that it is difficult to use with the more rigid and thicker tubing currently used for the heart-lung machine.

Currently, motors for roller pumps generate a peak torque of 70 in-lb which is equivalent to an outlet pressure of over 11,000 mmHg, or pressure that is over 35 times greater than the maximum pressure used clinically. This excessive torque can deform ⅜" ID with 3/32" wall PVC tubing placed in the roller pump if the outlet to that tubing is clamped.

It would be of great advantage to have tubing for peristaltic pumps that can provide one or more of the following characteristics: long pumping life, low spallation, self regulation, low power requirement, assure easy and accurate setting of occlusion, support an outlet pressure compatible with its use without affecting pumping, and reduce hemolysis. In addition it would also would be advantageous to have the tube made of material that is extrudable, allow inexpensive means to measure the pumped fluid pressures at the inlet and outlet of the pump without direct contact with pumped fluid, and allow flow control within the limits set for the inlet and outlet pressure of the pump. Such characteristics can be achieved with the present invention of extruded polyurethane tubing with at least one thin wall section when used with a conventional roller pump.

As part of an overall system to improve peristaltic pumping of blood, the present invention features a new innovative roller pump that takes advantage of the thin wall tubing as the pump tubing. As will be described hereinafter, the pump has a significantly higher pumping efficiency, lower power requirements, inlet and outlet pressure monitoring capabilities, flow regulation. The pumps would be safer, compact, require smaller batteries, lower power and be computerized and user friendly.

The thin wall tubing with the aforementioned advantages can also be used with peristaltic pumps used for intravenous fluid administration such as Flo-Gard 2000 made by Baxter Health Care or as described by many U.S. Patents, as for example, U.S. Pat. No. 4,702,675.

Presently there are two types of infusion pumps, the peristaltic pump using IV tubing, and the piston type pump that requires an expensive cassette (e.g. Flo-Gard 8500 made by Baxter-Travenol). The peristaltic pump is easy to control and use; however, the tubing used with it is almost exclusively made of polyvinyl chloride (PVC) with some limited use of silicone. This has the following disadvantages:

1. Both tend to spallate, abrading material from the tubing wall thereby releasing particles into the pumped fluid.

2. PVC loses its resilience over time (fatigue), thereby not returning to its original shape and resulting in an undesirable decrease in flow.

3. Relatively thick wall tubing is used (e.g. 0.100" ID with 0.140" OD resulting in a ID/Wall=5). Thick wall tubing requires peristaltic pumps that have higher torque motors to overcome the higher resistance to wall compression with most of the pump's energy being wasted on compressing the tubing wall. The relatively thick wall prevents accurate monitoring of the IV infusion pressure, which is used to alarm upon occlusion of said IV line by comparing that pressure to the pressure required for infusion. The thick wall also prevents accurate measurements of inlet pressure which is used to provide a low filling pressure alarm to indicate lower flow.

These problems were solved with the use of a cassette-type positive displacement volumetric pump (e.g. Baxter-Travenol's Flo-Gard 8500) but at a considerable expense: the cassette increases the costs of IV sets by 3 to 4 times. It would be of great clinical advantage to be able to overcome the above problems and measure the infusion pressure accurately with the less expensive disposable tubing used with peristaltic pumps such as Flo-Gard 6200.

Another positive displacement infusion system for IV administration which attempts to reduce power consumption of the pump and reduce costs is described by U.S. Pat. No. 4,846,637. This invention suggests using a specially formed pumping chamber comprised of an elastomeric material such as urethane or silicone with a first nondeformable portion of substantial thickness that provides strength and support during compression of said chamber and a second relatively thin deformable portion which forms an elliptical fluid conduit. Low power requirements are attributed to the thin wall and to its elliptical shape.

SUMMARY OF THE INVENTION

Briefly, the present invention provides designs that allow thin wall tubing to be used in peristaltic pumps. There are three major applications for the present invention: roller pumps used for extracorporeal circulation, peristaltic pumps used for IV infusion, and peristaltic pumps for industry. Pusher plate type pumps, as described for example by U.S. Pat. No. 4,239,464, can also be benefit from the invention. In the description of the invention hereinafter, extensive use is made of extracorporeal applications. This emphasis is made for description only. It should be understood that the described art is easily extended to the other aforementioned applications for peristaltic pumps.

The tubing of the present invention is comprised of a flexible thermoplastic polymeric tubular member (preferably medical grade Pellethane) that fits in a standard roller pump raceway (e.g. Sarns/3M Model 9000 Heart Lung Console) and which has at least one longitudinal portion of its wall thin. Sleeves or connectors at each end of the tubing provide the mechanical means to anchor the thin wall tubing and maintain it within the raceway. The tubing may be eccentric having a nonuniform cross section such that a portion of the circumference is "thick" and the opposite wall is thin. The thick wall supports the tube within the roller pump head and prevents it from kinking, stretching, or bunching. The thin wall collapses in response to decreasing inlet pressure thus providing self regulation to flow. The end connectors may also be designed to allow pressure measurement at the inlet and outlet of the roller pump without directly contacting blood. Pressure may also be measured directly by placing a pressure transducer against the indented thin walled section.

The objective of the present invention is to modify and improve tubing material and or profiles that provide regulation of pump flow in response to changes in inlet and/or outlet pressures.

It is another objective of the present invention to modify, improve and provide a tubing for use in peristaltic pumps that reduces hemolysis and allows for a simple technique to set the occlusiveness of the roller pump.

A further objective of the present invention is to make the tubing disposable, atraumatic, biocompatible, long lasting, with low-spallation, and with predictable and clinically useful pressure-flow characteristics.

A further objective of the present invention is to provide a new overall system that reduces the torque and power of the motor required for peristaltic pumps and either extends the life, or decreases the size of the batteries required for these motors.

A further objective of the present invention is to provide a pump tubing that allows the pump to be set in a very nonocclusive manner thereby reducing the maximum pressure and/or maximum suction that the pump can generate.

A further objective of the present invention is to limit the inlet and/or outlet pressures by redirecting the pump output to pump input via a recirculating line whenever inlet or outlet pressures become excessive.

A further objective of the present invention is to provide modifications of present peristaltic pumps that take advantage of the unique characteristics of the aforementioned pump tubing.

Other objectives, features and advantages of the present invention will become apparent by reference to the following detailed description of the presently preferred, but nonetheless illustrative, embodiments thereof with reference to the accompanying drawings therein:

BRIEF DESCRIPTION OF THE DRAWINGS

FIG. 3(a) is a transverse sectional view taken along lines 14 and 14' in FIG. 2(a) showing radial cross section of an eccentric thin wall tubing in an open state, whose ID and OD have a different centers;

FIG. 3(b) illustrates radial cross section as described in FIG. 3(a) showing the thin wall tubing in an occluded state;

FIG. 3(c) illustrates radial cross section as described in FIG. 3(a) showing the thin tubing semi-collapsed to control flow;

FIG. 4(a) is a transverse sectional view taken along lines 14 and 14' in FIG. 2(a) showing a radial cross section of another thin and thick wall tubing with a profile that provides channels for back flow of the pumped fluid when the thin wall tube is occluded;

FIG. 4(b) illustrates radial cross section as described in FIG. 4(a) showing the thin wall tubing in an occluded state;

FIG. 4(c) illustrates radial cross section as described in FIG. 4(a) showing the thin wall tubing semi-collapsed to control flow;

FIG. 5(a) is a transverse sectional view taken along lines 14 and 14' in FIG. 2(a) showing another possible radial cross sections of thin and thick wall tubing with a profile that provides channels for back flow of the pumped fluid when the thin wall tube is occluded;

FIG. 5(b) illustrates radial cross section as described in FIG. 5(a) showing the thin wall tubing in an occluded state;

FIG. 5(c) illustrates radial cross section as described in FIG. 5(a) showing the thin wall tubing semi-collapsed to control flow;

FIG. 6(a) is a transverse sectional view taken along lines 14 and 14' in FIG. 2(a) showing a radial cross section of thin wall tubing with a uniform wall in open state;

FIG. 6(b) illustrates radial cross section as described in FIG. 6(a) showing the thin wall tubing set nonocclusively;

FIG. 7(a) is a transverse sectional view taken along lines 14 and 14' in FIG. 2(a) showing a radial cross section of tubing 21 with uniform wall and two protrusions;

FIG. 7(b) illustrates radial cross section as described in FIG. 7(a) showing the thin wall tubing set occlusively;

Reference should now be made to the drawings wherein the same reference numerals are used throughout to designate the same or similar parts.

FIG. 1(a) illustrates a typical extracorporeal circuit in which the thin wall tubing of the present invention are used. The circuit includes a section of tubing 11 inserted at one end by means of a cannula (not shown) in the vena cavae for obtaining venous blood from the heart (not shown) of patient 2. Tubing 11 is coupled, as an example, to a collapsible venous reservoir 3 from which the blood is drawn by roller pump 4 and pumped through a membrane oxygenator 5 wherein oxygen is supplied to the blood and carbon dioxide is removed. The blood from the oxygenator is then conducted by means of tubing 13 to an arterial cannula (not shown) back to the patient. Blood spilling into the chest cavity (not shown) is collected via tubing 17 by suction generated by roller pump 6 and pumped into cardiotomy reservoir 7 from which it flows by gravity drainage through tubing 20 into venous reservoir 3. Another roller pump (not shown) similar to 6 can be also used to withdraw (vent) blood from one of the chambers of the heart such as the left ventricle. Similarly, another roller pump (not shown) similar to 4 can be used to pump cardioplegia to the cross clamped aorta (not shown).

Figure 8A:
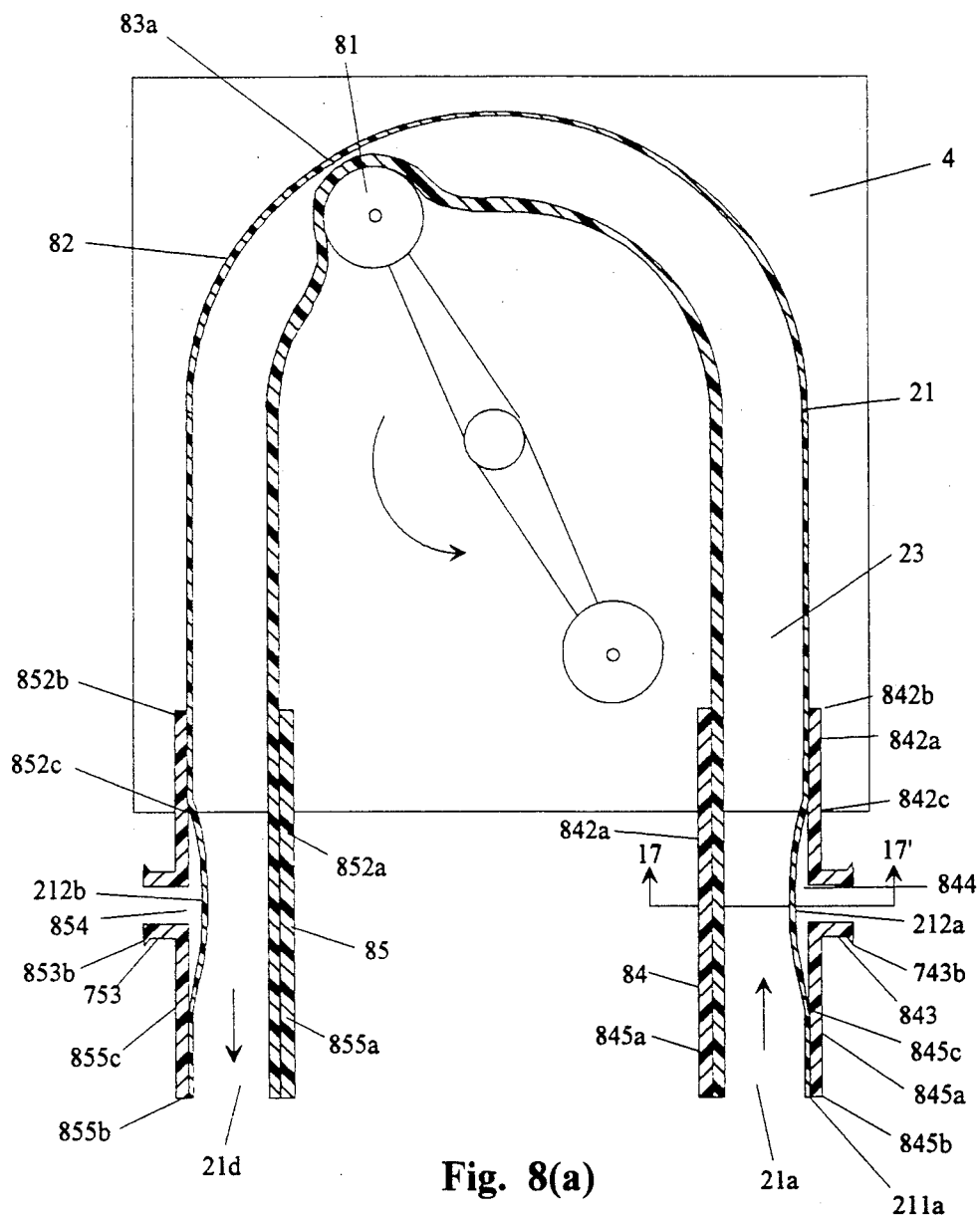
FIG. 8(a) is a longitudinal sectional view of a tubing placed in a roller pump with at least one thin wall, as described in FIG. 3(a), with adapter means designed to measure inlet and outlet pump pressure.
Figure 8C:
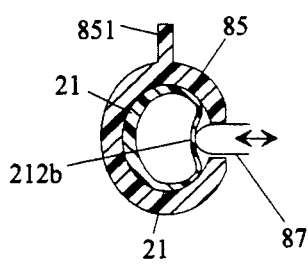
FIG. 8(c) is a radial cross section of adapter means of tubing described in FIG. 8(a) showing another method to measure fluid pressure noninvasively.
Figure 8B:
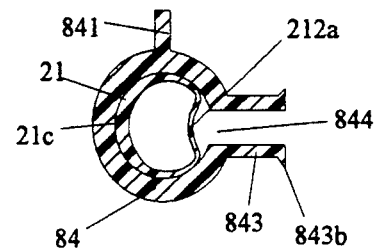
FIG. 8(b) is a radial cross section of adapter means of tubing described in FIG. 8(a) showing one method to measure fluid pressure noninvasively.

A thin wall tubing segment is placed in roller pump 4, an example of which is more fully illustrated in FIG. 8(b). As will be hereinafter explained in detail, this tubing prevents the generation of excess suction at the inlet to the pump and/or pressure at the outlet to the pump. The proper choice of material results in low spallation and extended pumping life of the tubing and the proper choice of cross section limits blood damage by assuring correct tubing occlusion. The pump tubing can also incorporate adapter means that allow measurement of pressure at inlet 4a and outlet 4b of roller pump 4. The pressures measured at 4a and 4b can be monitored by control unit 15, shown in FIG. 1(a) and better illustrated in FIG. 10(a). Should either pressure 4a or 4b exceed levels allowed by unit 15, as set by the user, the flow of pump 4 would either decrease or stop. A decrease in venous blood flow causes reservoir 3 to empty and collapse causing the obstruction of outlet port 3a and a decrease in inlet pressure 4a to roller pump 4. The reduced pressure, as will be described hereinafter, causes a reduction in the effective diameter of the thin wall tubing in pump 4 thereby reducing its flow. If the reduction in flow generated by pump 4 matches the reduced venous flow, then a new equilibrated state is established with no further decrease in inlet pressure. If the flow reduction is insufficient then the decreased pressure, sensed via the wall of thin wall tubing in pump 4, can be used to stop pump 4 as described above. Alternatively, if pump 4 provides for pressure control (e.g. Shiley's CAPS or that of the present invention illustrated in FIG. 9(b)), the reduced pressure would reduce the rotational speed of pump 4 until the pump flow matches the flow into reservoir 3. The combination of the collapsible reservoir and the thin wall tubing limiting negative pressure, requires a less sensitive regulation system for the roller pump and/or smaller blood reservoir 3.

Figures 10A, 10B:
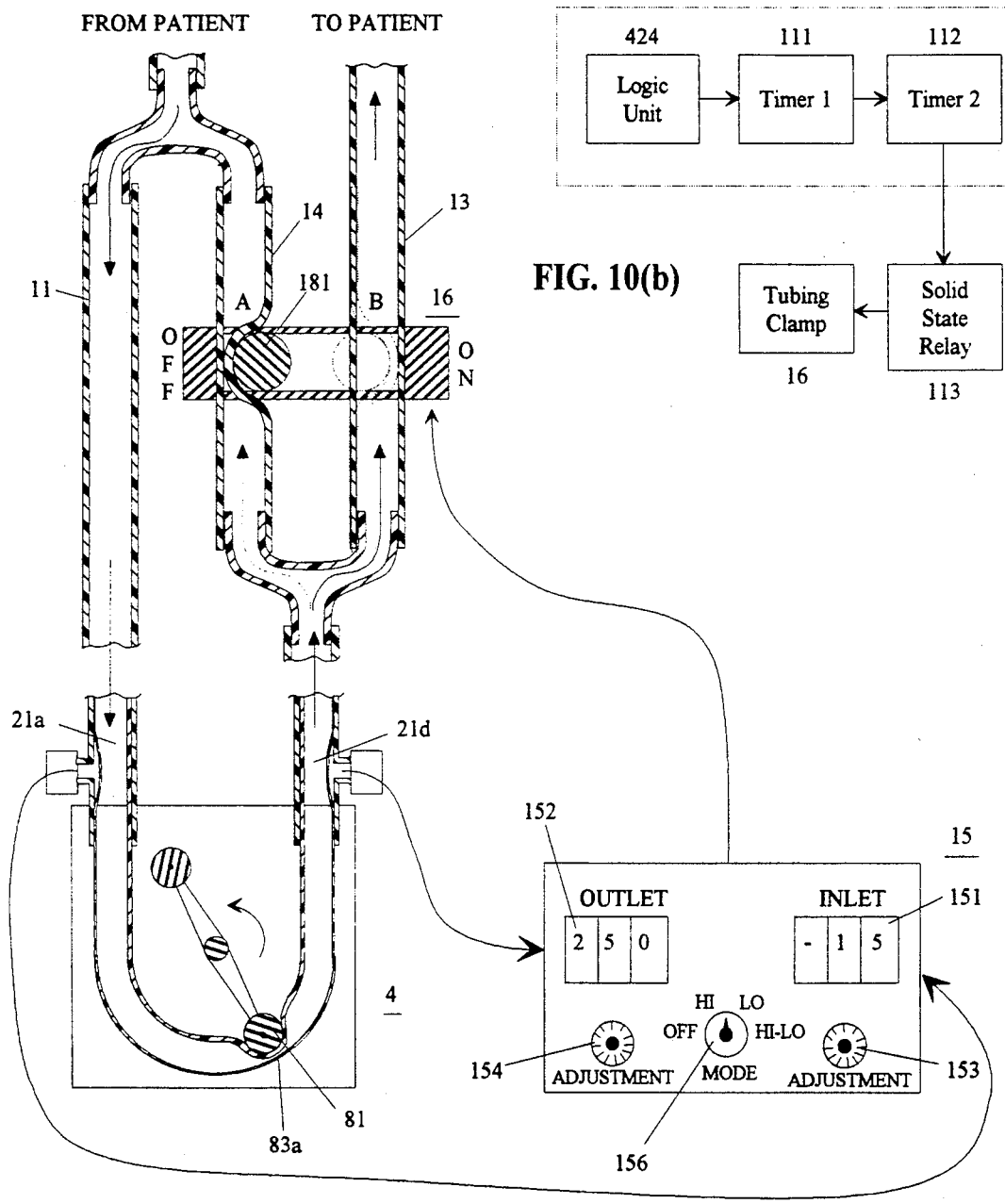
FIG. 10(a) illustrates a roller pump whose outlet and inlet pressures are measured and compared to values set by the user by a control unit. Said unit electrically controlling a tubing clamp that directs outlet flow to pump inlet via a recirculating line.
FIG. 10(b) is an illustration of a timing circuitry that can be incorporated into control unit 15 described in FIG. 10(a) to control the relative recirculation rate allowed by the tubing clamp also shown in FIG. 10(a)

Alternatively, the signal of unit 15 can drive solenoid actuated tubing clamp 16, more fully illustrated in FIG. 10(a), which directs outlet flow to inlet of pump 4 via recirculating line 14. Recirculating line 14 preferably connecting arterial line 13 to venous line 11 thereby increasing flow through oxygenator 5 to increase its gas exchange and decrease the likelihood of thrombus formation.

In a similar manner, utilization of a thin wall tube in suction pump 6 limits the negative pressure generated by pump 6. The degree of suction can be further controlled by either using nonocclusive setting with the pump tubing or using one of the special profiled tubes that provides channels, (e.g. 43a and 43b in FIG. 4(b)) as described hereinafter that allow backflow from outlet tubing 19 to inlet tubing 17 of pump 6. The channels have relatively high resistance to flow as compared to tubing 17 and 19 and under normal use the backward flow would only be a small portion of the forward flow. However, should thin wall tubing in pump 6 collapse excessively due to inadvertent occlusion of tubing 17 or the suction cannula (not shown) in patient 2, the forward flow would decrease significantly, approaching the backward flow thus preventing excess suction.

Figure 1A:
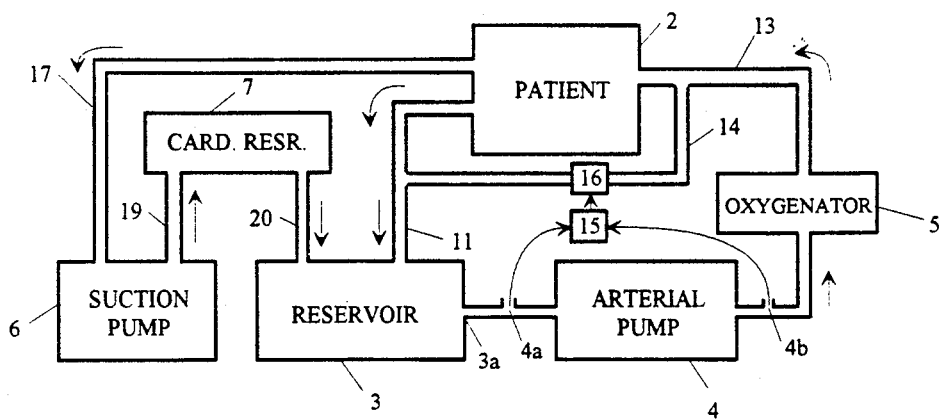
FIG. 1(a) is a schematic of a typical cardiopulmonary bypass circuit, which will be used to illustrate the various locations in which the invention may be used.
Figure 1B:
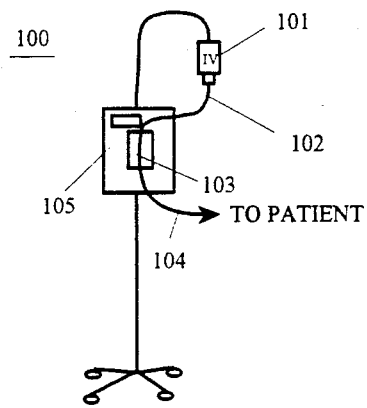
FIG. 1(b) is a schematic of a typical intravenous infusion setup illustrating another use for the invention.

FIG. 1(b) illustrates peristaltic pump 105 that delivers IV fluid from reservoir 101 to patient 2 via tubing 104. Tubing 103, made according to present invention, connected to standard IV tubing 102 at its inlet and standard IV tubing 104 at its outlet, is inserted into pump 105 and serves to pump said fluid. Thin wall tube 103 allows monitoring of the pressure generated by pump 105 and regulation of its flow to assure that infusion pressure does not exceed preset values by the user or manufacturer. Pressure sensing can be achieved as known in the art (e.g. pressure sensor 94 with spring biased plunger 95 described in U.S. Pat. No. 4,278,085) or in a similar manner as described in reference to FIG. 9(a) and 9(d). It may also be advantageous to use the present invention thin wall tubing to detect downstream occlusion as described in U.S. Pat. No. 4,373,525. That pump suggested using a tubing with an ID of 2.5 mm and a OD of 4.0 mm resulting in a ID/wall of 3.33. Use of a tube with the high ID/wall ratio provided by the present invention would dramatically increase the sensitivity of that system. Tube 103 can also be used to monitor inlet pressure to alarm the user should the inlet pressure be insufficient to fill tube 103. Because current state of the art tubing have low ID/wall ratio, they can be used only to measure inlet occlusion. The innovative thin wall tubing, as will be hereinafter described, has a sensitivity to changes in inlet pressure that is an order of magnitude higher. Thus, it can be used to detect inlet occlusion as well as the decrease in gravity feed from the solution reservoir 101. The latter offers an empty-container detector unavailable with current IV infusers utilizing tubing for pumping (e.g. Flo-Guard 6200).

Figure 2A:
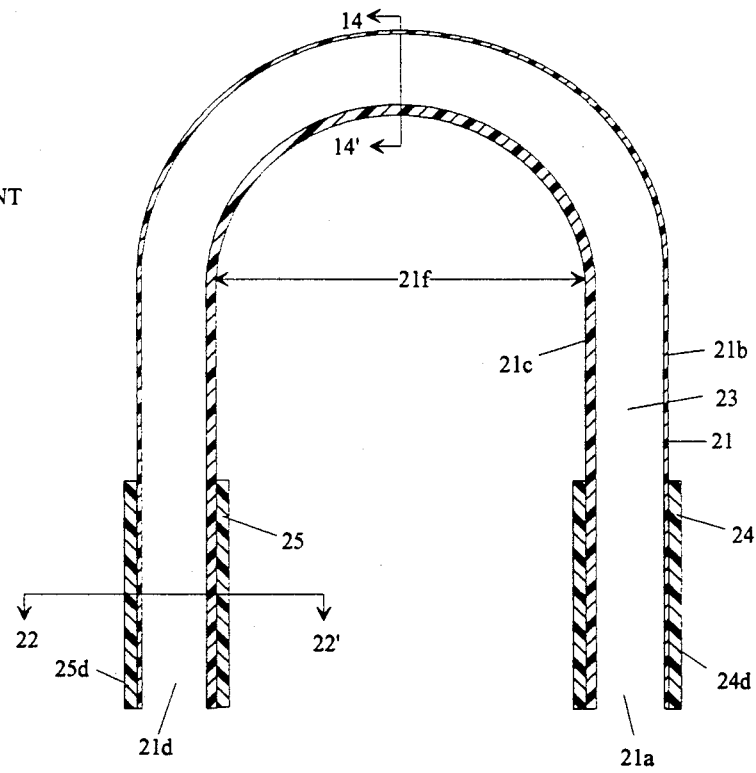
FIG. 2(a) is a schematic representation of a typical tubing according to the present invention, to be used with a roller pump, showing a longitudinal cross section of a tubing with at least one thin wall that includes a first and second adapter means.

FIG. 2(a) is a schematic of a longitudinal cross section of a typical tubing according to the present invention and FIG. 3(a) is a transverse sectional view taken along lines 14 and 14' in FIG. 2(a) showing one type of radial cross section of a thin wall tubing 21 with lumen 23 open. Other types of radial cross section according to the present invention are shown in FIGS. 4(a), 5(a), 6(a) and 7(a). Tubing member 21 preferably consists of a continuous length of blood compatible flexible polymeric material having a smooth fissureless inner surface throughout with at least a portion of its longitudinal wall being thin, with the ID to wall thickness ratio (ID/Wall) being at least 9. As with other pump tubing, tubing 21 serves to pump fluids when placed in peristaltic pumps. For example, in a roller pump, the pumping rate is a function of the number of times the roller passes over the tubing and the volume displaced within the tubing for each said pass. Because of thin wall 21b, the volume within tube 21 is sensitive to its transmembrane (transwall) pressure. Wall 21b preferentially starts to collapse from its natural shape when the pressure at inlet 21a reaches a critical pressure, Pc, below atmospheric pressure, as illustrated in FIG. 3(c) wherein thin wall 31b corresponds to thin wall 21b of FIG. 2(a), and is shown partially collapsed due to its internal pressure being below Pc. The critical pressure Pc for tube 21 depends on the material, the ratio ID/Wall, and the temperature of the wall. Pc for thinner wall 21b (31b in FIG. 3(a)) is closer to atmosphere than Pc for thicker wall 21c (31c in FIG. 3(a)). As long as the inlet pressure at 21a is higher than Pc, lumen 23 of tube 21 fills to at least its natural unstretched diameter as shown in FIGS. 3(a), 4(a), 5(a), and 6(a), and 7(a), and the flow rate is maximal for the set pump speed. When the inlet pressure at 21a drops below Pc, wall 21b begins to collapse, as shown in FIGS. 3(c), 4(c), and 5(c), by walls 31b, 41b, and 51b, respectively. The degree of said collapse depends on the difference between the pressure at inlet 21a and Pc. The collapse of wall 21b reduces intraluminal volume 23 within tube 21 causing a corresponding decrease in pump flow. By manufacturing tube 21 with different hardness and/or ratio of tubing ID to wall thickness it is possible to design tubes with different flow-pressure characteristics to meet different applications, a softer material or a larger ID/Wall ratio allows the tubing to collapse at a lower pressure difference. For example, in an extracorporeal circuit as illustrated in FIG. 1(a), when the venous cannula is connected directly to the pump inlet, inlet pressure 26 equals the height of the patient above the pump, less the pressure drop due to resistance to flow, plus any suction generated by the roller pump. If it is desirable to have a 50% change in flow due to the inlet pressure changing by 65 cm of $H_2O$ (e.g. the patient height above the pump, or 50 mmHg), then the flow sensitivity to inlet pressure should average 1.0% change in flow per mmHg change in inlet pressure at 21a. From the aforementioned equation relating ID/wall to flow sensitivity, (see "Description of the Prior Art"), it can be calculated that for a tube with a durometer in the 70 Shore A range, an ID/Wall=12 would have that flow sensitivity. All cross sections should be able to support an outlet pressure of at least 300 mmHg without affecting the pumping characteristics.

The thin wall tube, when used with some of the present prior art computerized pump consoles (e.g. Shiley's CAPS system), also allows greater flexibility in the feedback loops used to control the flow. Unlike standard tubing, the self regulation of flow and pressure measurements is inherent to the tube of the present invention and allows for simpler, more reliable pump control designs and therefore greater safety for the patient.

For the tube to collapse easily and also support pumping pressures used clinically, it is desirable that the tube be extruded, preferably from but not limited to, polyurethane elastomers, which have a much higher ultimate tensile strength, greater resistance to tear and abrasion than standard perfusion tubing. Polyurethanes also have greater resiliency, a property that allows the compressed tubing to return to its original shape, and therefore a thinner wall tubing of polyurethane can replace thicker wall polyvinyl chloride. Though polyurethanes are more expensive, the lower material requirements for the same applications compensates for the higher cost per pound. For medical applications the polyether-polyurethanes are preferable to the polyester-polyurethane. An excellent choice would be extrudable medical grade Pellethane 2363-75A, a polytetramethylene glycol ether polyurethane with a hardness of 72 Shore A (Dow Chemical Co. Midland, Mich. 48674). A thin walled tubing (0.375" ID by 0.030" wall, ID/Wall=12.5) extruded from Pellethane 2363-75, has a pumping life greater than 70 days, significantly greater than those reported under less demanding conditions for Tygon S-50-HL (2.3 days), silicone (2.3 days), and Super Tygon. S-65-HL (5.5 days). Another prime choice is Pellethane 2363-80A, a formulation with higher durometer and greater tensile strength than 2363-75A formulation. Thus for the same outlet pressure the former would require a thinner wall. It should be understood that as either the durometer or the ID/-Wall ratio increase, the tubing, when placed in a roller pump, has an increased tendency to kink within the pump head, a problem addressed hereinafter. For linear peristaltic pumps, also known as finger pumps this is not a consideration.

Another consideration in pump design is the torque required to generate the operating pressure (to be referred to as "pressure torque") relative to the torque required to overcome the elasticity of the tubing wall. The latter is required to squeeze and occlude the tubing within the pump head and will be referred to as the "tubing torque". The motor torque of pumps can be expressed in terms of in-lb, or in terms of the outlet pressure (mmHg) it can generate. The latter can be calculated by dividing the torque by the product of the internal cross sectional area of the tube and the radius of the pump head to be used. The larger the ratio of pressure torque to the tubing torque, the greater the pump efficiency. The initial torque required to rotate the head of a roller pump to overcome the elastic force of an empty Tygon Tube (S-50-HL) set occlusively is about 30 in-lb for a ⅜" ID by 3/32" wall, and about 15 in-lb for a ⅜" ID by 1/16" wall. In an identical setting the torque required with the thin wall tubing (Pellethane 2363-75, ⅜" ID by 0.030" uniform wall) is 0.75 in-lb, see Table 2. In Table 2 the torques are also expressed as the equivalent outlet pressure (mmHg) that the pump could generate with the torque required to squeeze the tubing. E-250 and E-500 are the calculated torques required to generate 250 and 500 mmHg respectively, expressed as a percentage of total torque. With the thin wall tubing the efficiency is 5 times greater at an output pressure of 500 mmHg and over 7 times greater at an output pressure of 250 mmHg. Higher efficiency translates to designs of pumps that are lighter, smaller, with lower power requirements, and smaller and or longer lasting batteries; attributes that contribute to more portable operations and reduced manufacturing costs. Similar results can be shown when comparing any standard tubing to a thin wall tubing with the same ID but with a larger ID/Wall ratio.

TABLE 2

| | | | Pump efficiencies for standard and thin wall tubing. | | | |
|---|---|---|---|---|---|---|
| Tubing Type | ID inch | Wall inch | ID/Wall | Tubing Torque in-lb | Tubing Torque mmHg | E-250 % | E-500 % |
| Std PVC | ⅜ | 1/16" | 6.00 | 30 | 3040 | 7.6 | 14 |
| Std PVC | ⅜ | 3/32" | 5.33 | 15 | 2680 | 8.5 | 16 |
| Invention | ⅜ | 0.030" | 12.55 | 0.75 | 135 | 64.8 | 79 |

ID — inside diameter. Wall — wall thickness; ID/wall — ID the tubing ID divided by tubing wall thickness; Tubing Torque — the torque required to overcome the tubing elasticity given in in-lb and as the outlet pressure (mmHg) that can be generate by the torque; E-250 and E-500 — the efficiency of the pump taken as the torque used to generate outlet pressure expressed as the percentage (%) of the torque applied by the rollers of the pump to the tubing. The data is applicable for an American Optical 5" roller pump head at room temperature.

FIG. 3(a) is a transverse sectional view taken along lines 14 and 14' in FIG. 2(a) showing radial cross section of tubing 21 with a uniform ID and OD but with the respective centers of the ID and OD eccentric. FIG. 3(b) is a sectional view of tubing 21, as described in FIG. 3(a), showing its radial cross section completely occluded in a proper manner. To assure proper occlusion, it is necessary that the occluder of the peristaltic pump (e.g. the roller of the roller pump) occlude the tubing uniformly throughout its compressed section, as shown in FIG. 3(b). This forms a linear geometric axis parallel to both the thickest and thinnest wall when said tubing is occluded. The symmetry of tubing 21 shown in FIG. 2(a) with cross section 31, shown in FIG. 3(a), dictates that when the thinnest wall, 31b, is compressed against the thickest wall, 31c, the sum of thicknesses of the two opposite walls is constant along entire cross section 31. Thus, when placing tubing 21 in peristaltic pump 4 (e.g. the roller head), the tubing must be oriented to assure that said linear geometric axis is perpendicular to the axis defined by the direction of occlusion. That is the geometric plane common to both the thickest, 21c, and thinnest, 21b, walls is perpendicular to the occlusion of the tube, as shown in FIG. 8(a). This can be achieved with adapter means 24 and 25 each incorporating a directional anchor as illustrated for adapter 25 by 25a shown in FIG. 2(a) and directional anchors 841 and 851 a shown FIG. 8(a). The aforementioned anchors maintain tubing 21 in the roller head in a predetermined orientation by clamping down on the extended profile of anchors 24a at pump inlet 21a and 25a at the pump outlet 21d via the standard tubing clamps associated with roller pump heads. As is obvious to those practicing the art of perfusion, FIG. 3(b) is for illustration only and, to prevent blood damage, the two opposite inner walls would not meet but rather have a small space therebetween. To assure accurate flow when pumping non-blood products, the complete occlusion as illustrated in FIG. 3(b) is desirable.

The ratio of thin wall 21b to thick wall 21c depends on distance 31e, shown in FIG. 3(a), between the center of the ID and the center of the OD of tube 21 with cross section 31. Thus, for any size tubing, walls 31b and 31c could be adjusted during extrusion by simply moving the center pin relative to the extruder without requiring special tooling.

Figure 2B:
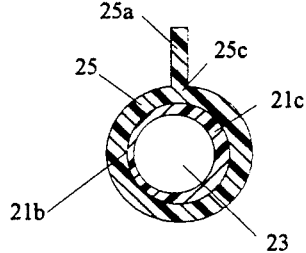
FIG. 2(b) is a radial cross section along the adapter means (end connector) illustrated in FIG. 2(a)

Adapter means 24 and 25, as shown in FIG. 2(b) for example, can be made of a cylindrical sleeve made of polyvinyl chloride whose ID equals the OD of the thin wall tube 21. Sleeve 24 and 25 are secured (e.g. adhesive, solvent bonding or impulse heating) over, for example, the first 3 to 5" length of the inlet 21a and outlet 21d of thin wall tubing 21 respectively. The additional thickness of sleeves 24 and 25 at ends of the thin wall tubing provide 1) mechanical support to prevent the thin wall tubing, extending outwardly at the inlet and outlet of the roller head, from accidentally kinking; 2) the mechanical support required to clamp the tubing within the roller pump header by the tubing clamps; and 3) the stiffness at the end of said thin wall tubing to enable the user to facilitate coupling of perfusion connectors into inlet 21a and outlet 21d of the thin wall tubing 21 and integrate it into a perfusion circuit. Proper alignment of tube 21 can also be achieved by marking adapter means 24 and 25, as for example with color stripe 25c incorporated into wall 25 shown in FIG. 2(b), which could replace directional anchor 25a. Another feature of these circular sleeves is that they allow easy adjustment of the tension placed on the thin wall tubing between the inlet and outlet clamps. For extracorporeal circulation, it is advantageous to form the adapter means with an outside diameter equal to the OD of a standard perfusion tubing (e.g. ½, 9/16, 11/16). This facilitate mounting said adapter means to standard clamps of the roller pump.

Since roller pumps have U-shaped heads it is important that the natural curvature of the tubing be parallel to the plane that intersects the thinnest, 21b, and thickest, 21a, sections. For example the diameter of the "natural" curvature of tube 21 shown in FIG. 8(a) could be formed to match the inside diameter of raceway 82 of the two popular size roller pump heads, 4"-5.5" and 5.5"-7". The curvature can be set with the thinnest 21b or the thickest 21c section along the outside of the curvature the pump head. This can be achieved immediately after extrusion by allowing the tubing to set in a predetermined orientation and curvature. It also would be advantageous to extrude thin wall tube 21 with internal diameters that equal standard sized tubing for their respective uses. Thus, for example, for cardiopulmonary bypass tubing would be extruded with IDs of ¼, ⅜, and ½".

To reduce the tendency of roller 81 of pump 4 illustrated in FIG. 8(a), to stretch tube 21 along said roller direction of rotation (i.e. walking), a lubricant such as silicone can be applied to the outside of the thin wall tubing 21, particularly on those polyurethanes with a high coefficient of friction.

FIG. 4(a) is a transverse sectional view taken along lines 14 and 14' in FIG. 2(a) showing another possible radial cross section of tubing 21, 41, with a uniform external circumference and a non uniform internal lumen with thin wall section 41b continuous with thick wall section 41c. Thin wall 41b, defined by angle 49, being between 185° and 355° of the circumference. Thus, when tube 41 occludes properly, as shown in FIG. 4(b) and as achieved by methods previously described in reference to cross section 31 in FIG. 3(b), channels 43a and 43b are formed. The size of said channels is dictated by the difference between wall thickness 41a and 41c and the circumferential ratio of the thick wall 41c to thin wall section 41b. These channels allow backflow between the outlet 21d and inlet 21a of the pump that limit excess inlet and/or outlet pressure and may achieve pressure flow characteristics similar to present prior art pumping systems, but without requiring the special contoured rollers. The channels also reduce the stresses along bent edges 44 and 45. Even when tube 21, with cross section 41, is completely compressed (occlusive setting of roller pump 4) with wall 41b contacting wall 41c, edges 44 and 45 are bent less than 180°.

FIG. 4(c) illustrates cross section, as described in FIG. 4(a), during flow regulation when inlet pressure 21a is below Pc of thin wall 41b, as previously described with respect to FIG. 1(a). For pumping blood it may also be advantageous to have thick section 41c very narrow, as for example 0.015" to 0.050", and with a thickness that is greater than that of 41b by 0.010" to 0.050". Said dimensions would provide a protrusion that prevents the opposite walls from contacting except at the protrusion. Thus, tubing 21 could be set "occlusively" with the aforementioned spring actuated roller (e.g., as made by Cobe Laboratories or as will be described with respect to FIGS. 9(b) and 9(c)), while maintaining throughout the circumference, except at 41c, a nonocclusive setting.

FIG. 5(a) is a transverse sectional view taken along lines 14 and 14' in FIG. 2(a) showing another possible radial cross section of tube 21, 51, with a uniform internal lumen and a non uniform external circumference with thin wall section 51b continuous with thick wall section 51c. The thin wall portion, defined by angle 59, being between 185° and 355° of the circumference. Thus, when tube 51 occludes properly, as shown in FIG. 5(b) and as achieved by methods described previously for cross section 31 illustrated in FIG. 3(b), channels 53a and 53b are formed. The size of channels 53a and 53b is dictated by the difference between wall thickness 51b and 51c and the circumferential ratio of the thick wall 51c to thin wall section 51b. These channels allow backflow between the outlet 21d and inlet 21a of the pump that limits excess inlet and/or outlet pressure and may achieve pressure flow characteristics similar to the aforementioned prior art pumping system without requiring special contoured. The channels also reduce the stresses along bent edges 54 and 55. Even when tube 51 is completely compressed (occlusive setting of roller pump) with wall 51b contacting wall 51c, edges 54 and 55 are bent less than 180°. It may also be advantageous to have thick section 51c very narrow, as for example 0.015" to 0.050", and with a thickness that is greater than that of 51b by 0.010" to 0.050". Said dimensions would provide a protrusion that prevents the opposite walls from contacting except at said protrusion. Thus, tubing 21 could be set "occlusively" with the aforementioned spring actuated roller, and as will be described with respect to FIGS. 9(b) and 9(c), while maintaining throughout the circumference, except along 51c, a nonocclusive setting.

It should be understood to those familiar in the art of perfusion that cross section 51 with its uniform inner cross section can be used with standard perfusion connectors and may provide better flow conditions than cross section 41 illustrated in FIG. 4(a).

FIG. 5(c) illustrates cross section 51 in a semi-collapsed state controlling flow when inlet pressure 21a is below Pc, as previously described with respect to FIG. 1(a).

FIG. 6(a) is a transverse sectional view taken along lines 14 and 14' in FIG. 2(a) showing another possible radial cross section of tubing 21, 61, with a uniform outer and inner diameter and uniform thin wall 61b, said wall having an ID to wall ratio of at least 9. When tube 21 with cross section 61 is set nonocclusively, as shown in FIG. 6(b), channels 63a, 63b and 63c are formed. The size of said channels is dictated by the degree of occlusion set by the user of the pump. This is illustrated with respect to FIG. 8(a) with roller 82 of roller pump 4 squeezing tube 21 in a nonocclusive manner to form a similar channel 83a. These channels limit the excess inlet and/or outlet pressure, in a manner similar to that described with respect to FIG. 4(b) and FIG. 5(b). Note that when the tubing is set nonocclusively, the center portion 63c of tubing 21 may still make contact with the opposite wall, as illustrated in FIG. 6(b), a condition that can increase hemolysis.

Another advantage of high ID/wall is that the absolute manufacturing or extrusion tolerances of extruded wall thickness 61b is better with thin wall than with thick wall, said lower variation in wall thickness results in more precise occlusion setting, lower hemolysis, and better flow control.

FIG. 7(a) is a transverse sectional view taken along lines 14 and 14' in FIG. 2(a) showing another possible radial cross section of tubing 21, 71, designed to reduce wall contact inherent to standard tubing as depicted in FIG. 6(b) along channel 63c. The configuration in FIG.

7(a) and FIG. 7(b) will also increase pumping life, provides backflow channels, and is suitable for use with spring actuated rollers that occlude the tubing. Two inner ribs or protrusions, 71c and 71d, are formed continuously in a longitudinal manner with the inside circumference of wall section 71b. These protrusions support the center section of wall 71b and prevent its contact with the opposite wall except at the tip of said protrusions. Said protrusions can have a width of, for example, 0.015 to 0.050″, a height, for example, of 0.010″ to 0.050″, and be placed approximately $\pi D/6$ apart, where D is the inner diameter.

FIG. 7(b) depicts tube 21, with the cross section 71 described in FIG. 7(a), occluded properly and forming three channels, 73a, 73b, and 73c. The size of said channels is dictated by the location and dimensions of said protrusions, degree of occlusion, and inside diameter of tubing. Channels 73a, 73b and 73c allow backflow between the outlet 21d and inlet 21a of pump 4 that limits excess inlet and/or outlet pressure and may achieve pressure flow characteristics similar to the aforementioned Rhone-Poulenc pumping system without the special contoured rollers required for the latter. As with cross sections 31, 41 and 51 illustrated in FIGS. 3(a), 4(a), and 5(a) respectively, channel 73a and 73c also reduce the stresses along bent edges 74 and 75. Even when cross section 71 is completely compressed (occlusive setting of roller pump 4) with protrusions 71c, 71d contacting wall 71b, edges 74 and 75 are bent less than 180°.

Cross section 71 can be used with roller pumps designed with aforementioned spring actuated roller occlusion mechanism without over occluding the tubing. Hemolysis would be reduced because wall contact is limited to the small width of the protrusions. Thus, for a $\frac{3}{8}$″ ID tubing the circumferential contact of the opposite wall is limited to 5% with 0.015″ wide protrusions and to about 16% with 0.050″ wide protrusions, as compared to up to 100% with tubing without protrusions. It should be obvious to those skilled in the art that aforementioned inner longitudinal ribs 71c and 71d can instead be formed longitudinal outward along the outside diameter much like the single thick wall section 51c described in FIG. 5(a) is comparable to thick wall section 41c described in FIG. 4(a).

The combination of a polyurethane tubing 21 formed with said protrusions and a large ratio of ID/wall results in a tube with unique pumping characteristics: it requires low force to compress tubing wall to said nonocclusive state, prevents over occlusion, reduces the folding of walls along creases (e.g. 75 and 74 in FIG. 7(b)) thus reducing compressive and tensile stresses at the fold line. This extends the tubing pumping life, and allows the use of pump with the occlusion set by spring actuated roller, as described with reference to FIG. 9(b) and 9(c).

The extended pumping life, the response of tubing wall to inlet pressure, and the low power requirements allows the tubing to be pumped at a significantly higher rate than standard tubing. Thus, even if the tubing is set so nonocclusively that it would significantly affect the flow, the flow could be maintained by increasing the pump speed. With a thick wall tubing the pump speed would be limited by the ability of the tubing to return to its noncompressed shape. The relatively low inlet pressure would not affect that return. With the thin wall tubing, the inlet pressure also serves to maintain the tubing open. Calibration curves relating the flow to degree of occlusion, pump speed, inlet and outlet pressures and to the pump speed, as is the case with centrifugal pumps, could be used to determine flow. As will hereinafter disclosed with respect to FIGS. 9(a), 9(b), 9(c), and 9(d), a novel pressure sensor probe and logic circuit may also be used to develop and determine the flow rate. Alternatively, an ultrasonic (e.g. Transonic Corp.) or magnetic flow probe could also be used.

It should be understood by those skilled in the art of perfusion that proper alignment of tube 21 with the asymmetric cross section described in FIGS. 7(a) and 7(b) can be achieved by the same principals described with respect to cross sections shown in FIGS. 3(a), 4(a), and 5(a). It should also be understood that cross section 71 may be used with standard tubing to assure non occlusiveness. For example, in dialysis the blood flows are low, the pump speed is relatively slow, the tubing is relatively soft, and often, the occlusion mechanism used is the aforementioned spring actuated roller. By incorporating the protrusions described in FIG. 7(a) the degree of hemolysis would be reduced even if ID/Wall ratio is below 9.

FIG. 8(a) is a longitudinal sectional view of thin wall tubing 21 placed in pump 4 with adapter means 84 and 85, and further designed to facilitate the measurement of fluid pressure within tube 21 at inlet 21a and outlet 21d. As illustrated in FIG. 8(a), the thin wall portion allows the tubing to transmit the intraluminal pressure across the thin wall. For example, using cross section 31, shown in FIG. 3(a), adapter means 84 seals thin wall tube 21 along its circumference between 845b and 845c and between 842b and 842c but not between 842c and 845c to form chamber 844 sealing section 212a of thin wall 21b. Similarly, adapter means 85 seals thin wall tube 21 along its circumference between 855b and 855c and between 852b and 852c but not between 852c and 855c to form chamber 854 sealing section 212b of thin wall 21b. The seals can be formed by adhesive, heat sealing, or other conventional sealing techniques known in the art and appropriate to the materials used. Tubing 21, illustrated in FIG. 8(a), can have any of the cross sections shown in FIGS. 3(a), 4(a), 5(a), 6(a) and 7(a).

FIG. 8(b) is a sectional view of tubing 21 taken between lines 12 and 12′ of FIG. 8(a), using as an example cross section 31 previously described in FIG. 3(a). When wall portion 21b of tube 21 is made sufficiently thin and with minimal elastic memory, then the portion illustrated at 212a can be used to transfer the pressure of the pumped fluid at inlet 21a to chamber 844. The pressure at inlet 21a may be measured via port 843 in communication with chamber 844 with an electronic pressure transducer as will be further described with respect to FIG. 10(a). Similarly, section 212b can be used to transfer the outlet pressure of the pumped fluid at 21d to chamber 854 from which, for example, the pressure may be measured via port 853 with another electronic pressure transducer. The volume change in chamber 844 or 854 useful for pressure transfer is equal to the respective volume change caused by the wall of region 212a or 212b when it moves from an indented state, shown in FIG. 3(c), to its natural, nonindented state shown in FIG. 3(a). The effects of the motion of the wall, as it transfers the pressure signal, should not cause a significant effect on the accuracy or fidelity of the measured pressure signal. Either positive or negative pressures can be sensed. Adapter means 84 and 85 are generally cylindrical, nonelastic in construction, and molded from thermoplastic material such as clear polycarbonate, polyvinyl chloride, polyethylene or the like. As depicted, chambers 844 and 845 have a relatively low volume. In practice these volumes should not be greater than the acceptable indentation of sections 212a and 212b respectively. The fluid used to transmit pressure from chambers 844, 854 to a pressure transducer, not shown, can be a liquid such as normal saline or gas such as air. With the latter, the total volume of chambers 844 and 854, the volume of the interconnecting tubing (not shown) and the volume required by the pressure transducer should be limited to assure that volume change afforded by the respective motion of thin walls 212a and 212b is greater than volume change required by the pressure transducer. To assure high fidelity of the pressure measured in chamber 844 and chamber 845, and to avoid thin wall section 212a from expanding against housing 84 and section 212b from expanding against housing 85, thereby saturating pressure transfer, it is advantageous to use liquid as a pressure transfer agent in chamber 844 and 854. The use of a sterile physiological solution has the added advantage of providing an acceptable environment to blood should the thin wall develop a leak. For medical applications it is advantageous to form ports 843 and 853 with standard female luer fitting 843b and 853b respectively.

The combination of thin section 212a and housing 84 or 212b and housing 85 can replace devices such as PMS-3 Pressure Monitor Separator (Healthdyne Cardiovascular Inc. Costa Mesa, Calif.) These prior art devices attach to prior art "T-connectors" in the blood line. Replacing a "T-connector" with an inline pressure transfer device has the advantages of eliminating stasis conditions which can promote thrombus formation, reducing costs, and simplifying the pressure monitoring set up required. As with such prior art devices, the pressure signals from port 843 and 853 can be used to turn the roller pump on and off or, if pump 4 is designed with inlet and outlet pressures (e.g. Shiley's CAPS) controlling flow, via controlling pump speed as previously described with respect to FIG. 1(a).

The adapter means 84 and 85 are also used to secure thin wall tube 21 within the raceway of peristaltic pump 4. Sections 845a and 855a of adapter means 84 and 85 respectively provide mechanical support to tube 21 at 21a and 21d to enable the user to connect the thin wall tube to the pumping circuit. Connectors 84 and 85 may incorporate directional anchors 841 and 851 respectively which are identical in design and function as anchor 25a described in reference to FIG. 2(a) and FIG. 2(b).

FIG. 8(c) illustrates an adapter means identical to 84 or 85 except that it is designed for a tubing assembly that includes a transducer means to measure fluid pressure within said tubing by having a pressure sensor making direct contact with thin wall 21b. For that purpose, chamber 844 is exposed to the outside without fitting 843 shown in FIG. 8(a) and 8(b). Deformation of exposed thin wall section 212b makes direct contact with moving element 87, said element motion actuating a transducer to generate a pressure signal. The pressure signal can be obtained in any one of many ways as known in the art of pressure transducers and as better illustrated in FIGS. 9(a), 9(b), and 9(c). For both connectors the pressure measuring means must measure pressure within the allowed motion of walls 212a and 212b respectively, as described previously. The pressure signal thus sensed can be used to control the pump flow. This is easily accomplished in as much as the thin wall tubing used to pump the blood is designed to collapse as inlet pressure becomes excessive. Thus, the thin wall tubing can control flow within certain limits. When those limits are exceeded and sensed, the speed of the pump can be reduced to better match the inlet flow.

The significantly higher pump efficiency, lower power requirements, the inlet and outlet pressure monitoring capabilities, and the auto flow regulation due to the collapse of the thin wall tubing in response to decreased inlet pressure allows the design of a new class of peristaltic pumps. These pumps are designed to take advantage of the unique characteristics of said thin wall tubing, as known in the art, incorporate means for sequentially occluding said thin wall tubing to pump a fluid therethrough with at least a pair of peristaltic pressure members actuated by a single rotating member. These new pumps provide additional safety features and automation not available with present pumps and enable the design of new pumps which require lower power, with smaller longer lasting batteries. The pump may be computerized, user friendly, and compact.

Figure 9A:
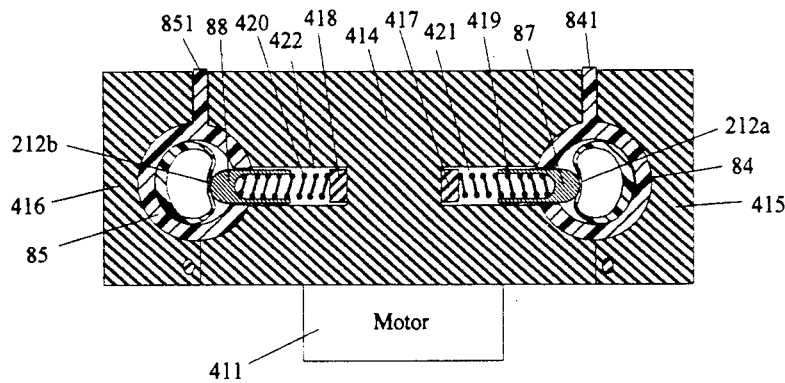
FIG. 9(a) is one view of a schematic of a roller pump according to the present invention.
Figure 9B:
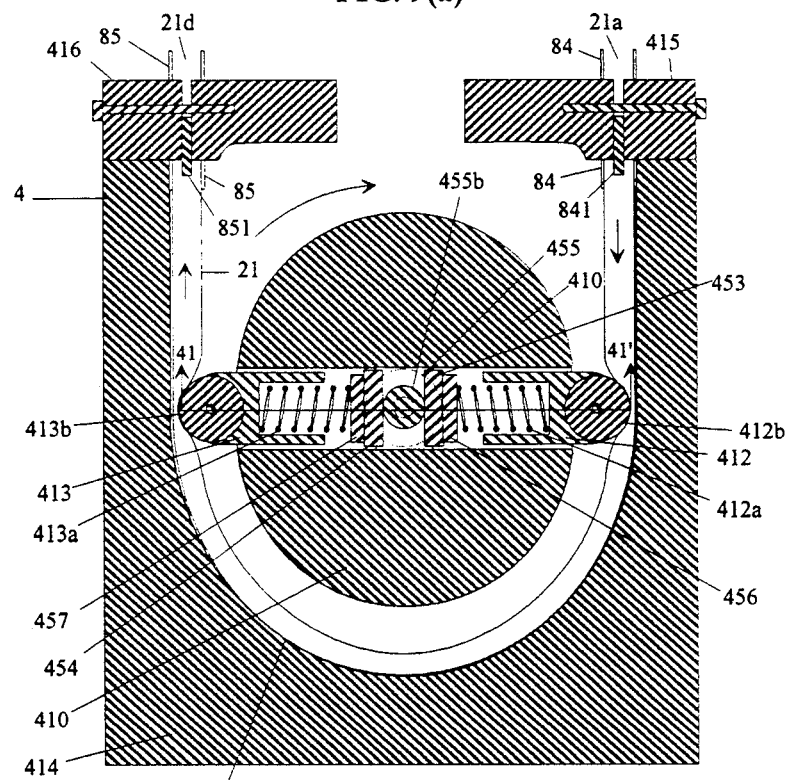
FIG. 9(b) is a top sectional view of the roller pump illustrated in FIG. 9(a)

FIGS. 9(a), 9(b), 9(c), and 9(d) illustrate a peristaltic roller pump according to the present invention designed to take advantage of the unique characteristics of said thin wall tubing. The pump is similar to other roller pumps, and includes as pressure members a pair of rollers (tubing rollers 412b and 413b) mounted for reciprocation along a single rotating axis, and variable speed motor 411 shown in FIG. 9(a) which rotates, via shaft 410b, pump head 410, shown in FIG. 9(b). As illustrated in FIG. 9(b), the pump head and tubing rollers 412b and 413b incorporated in it are centered in pump head raceway 414, said raceway providing curved surface 414a against which rollers 412b and 413b press tubing 21 to appropriately occlude tube 21. Curved surface 414a is described by a circle whose center coincides with the center of rotation of rollers 412b and 413b. Tubing clamps 415 and 416 retain tubing 21 about its adapter means 84 and 85. The features that distinguish pump 4 from existing prior art roller pumps are described below.

As illustrated in FIG. 9(a), roller pump 4 incorporates two noninvasive pressure sensors 417 and 418. Said pressure sensors can be pressure transducers which operatively engage said thin wall tubing at said inlet and said outlet. Noninvasive pressure sensor 417 opposite clamp 415 communicates via moving element 87 with thin wall 212a of tube 21. Noninvasive pressure sensor 418 opposite clamp 416 communicates via sliding element 88 with thin wall 212b of tube 21. Pressure sensor 417 and element 87 are housed in cylindrical cavity 421 and pressure sensor 418 and element 88 are housed in cylindrical cavity 422. These cavities are incorporated in pump head raceway 414. For proper function element 87 indents thin wall section 212a within connector 84 and element 88 indents thin wall section 212b within connector 85. To provide better design flexibility said pressure transducers can be reciprocally mounted and resiliently biased into engagement with said thin wall tubing. For example, spring 419 is placed between sliding element 87 and pressure sensor 417 and spring 420 between sliding element 88 and pressure sensor 418. For both pressure sensors, a "zero" signal can thus be obtained before priming tube 21 with a liquid, in which the pressure due to the elastic force of walls 212a and 212b is nulled.

During negative pressure measurements the elastic force of the wall would resist further indention and thus the measured pressure would be underestimated. During positive pressure measurements the elastic force of the indented wall would add to the pressure within tube 21 that pushes the wall outward and thus the measured pressure would be overestimated. To overcome these effects of the elastic wall, electronic logic controller unit 424 that interfaces sensors board 423 with front panel display 425 illustrated in FIG. 9(d) incorporates a logic circuit that allows the calibration of sensors 417 and 418. With tube 21 in place in pump 4, as illustrated in FIG. 9(b), the pressure at inlet 21a sensed by sensor 417 would be exposed to atmospheric pressure (to zero the sensor), a negative pressure, and a positive pressure. For each of the three pressure conditions, the appropriate control knob of front panel 425 would be used to set inlet pressure meter 433 to the known respective pressures. Thus, knobs 426, 427, and 428 would be set for the negative, zero, and positive pressures respectively. Once set, logic unit 424 would incorporate these settings to provide meter 433 of display unit 425 shown in FIG. 9(d) with a calibrated pressure signal that minimized the aforementioned effects of the elastic wall. For best calibration, the negative and positive pressures should be within the acceptable operating conditions.

Pressure sensor 418 which measures pressure at outlet 21d as shown in FIG. 8(a), and FIG. 9(a), is required to sense only positive pressure. Thus, with tube 21 in pump 4, as illustrated in FIG. 9(a), the pressure at outlet 21d sensed by sensor 418 would be exposed to zero, and a known low and high pressures. For each of these three conditions, the appropriate control knob of the front panel of the display/control unit 425, shown in FIG. 9(d), would be used to set outlet pressure meter 434 to the known respective pressures. Thus, knobs 429, 430, and 431 would be set for the zero, low and high positive pressures respectively. Once set, logic unit 424 would, as known in the art, incorporate these settings to provide meter 434 with a calibrated pressure signal with minimal effects due to the elastic wall. For the best calibration, the low and high positive pressures should be within the acceptable operating conditions, as determined or set by the user.

Figure 9C:
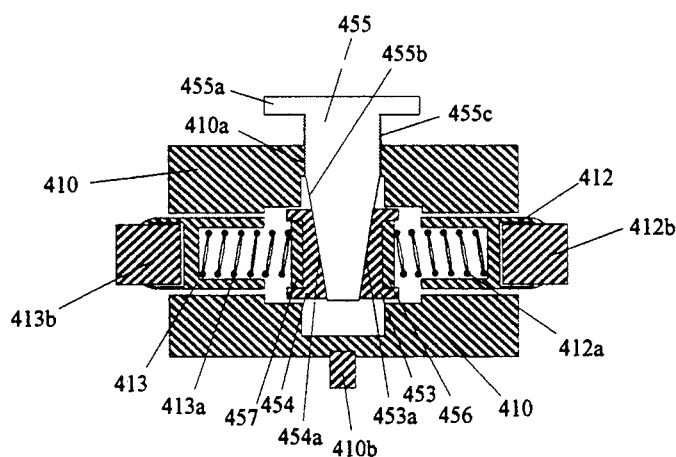
FIG. 9(c) is transverse sectional view taken along lines 41 and 41' in FIG. 9(b) showing a cross section of the roller head with adjustable spring loaded rollers and sensors that determine the degree of occlusion.
Figure 9D:
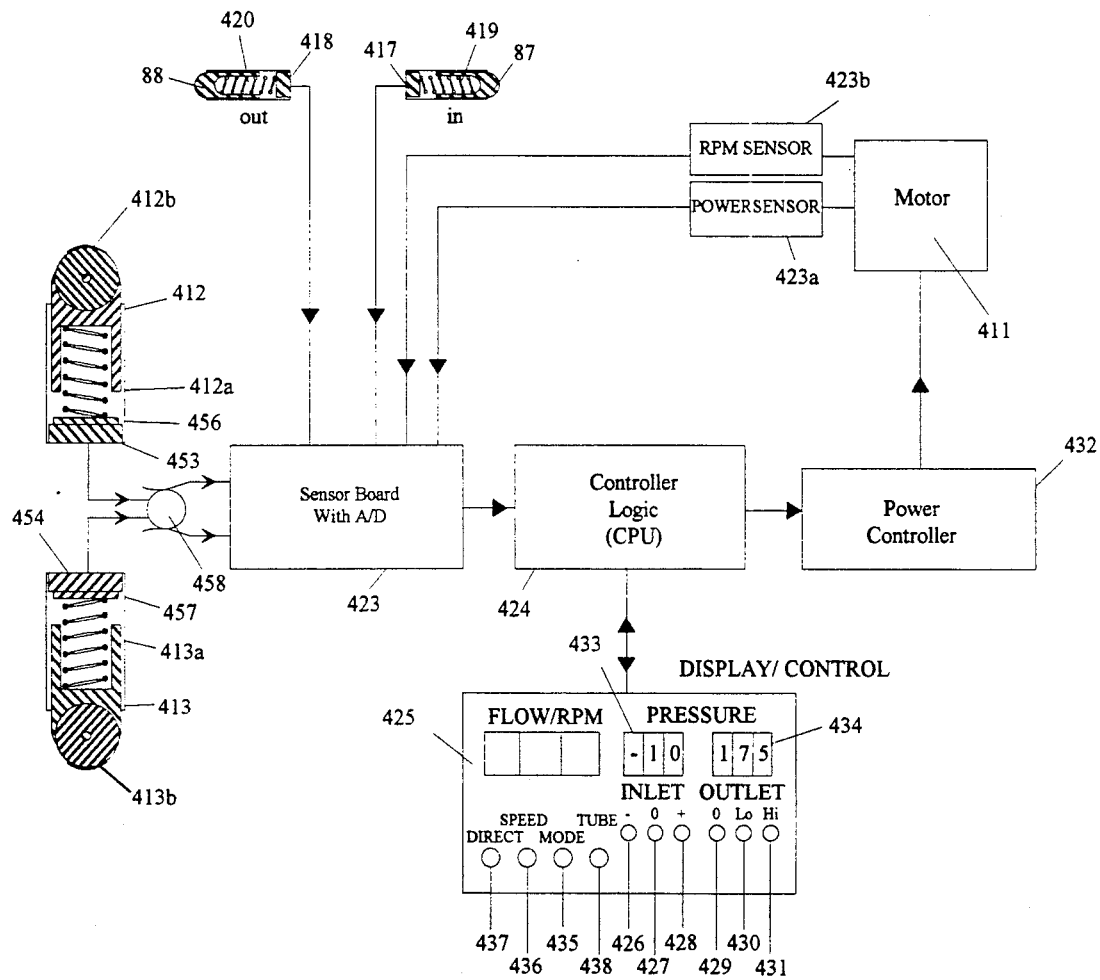
FIG. 9(d) is a block diagram illustrating the control and display unit for the roller pump illustrated in FIG. 9(b)

In the present invention motor 411, illustrated in FIG. 9(a) and 9(d), may be a much lighter and smaller version of other motors used for roller pumps with the same pumping capabilities. Thus, for example, for roller pumps used for cardiopulmonary bypass, instead of having a peak torque of 70 in-lb, motor 411 can have a peak torque of 10 in-lb or less. In addition, as described in reference to Table 2, at least 40% of the power supplied by motor 411 is used to generate an output pressure of 250 mmHg.

For an occlusively set roller pump, the flow is a direct function of pump speed. If the roller pump is used to pump blood, it may be set very nonocclusively, or if the pump tubing is sensitive to outlet pressure, as the present invention intends and as will be described hereinafter, the flow becomes a function of pump speed and inlet and outlet pressures of the pump. Since with the present invention both can be measured noninvasively, flow can be determined from equations relating flow to the inlet and outlet pressures for each of the cross sections shown in FIGS. 3(a), 4(a), 5(a), 6(a) and 7(a). These equations can be programmed into control logic 424 shown in FIG. 9(d) for roller pump 4 illustrated in FIG. 9(a) and 9(b). Thus, for example, in FIG. 9(d), sensing circuit 423, in communication with logic unit 424, can translate from calibration curves inlet pressure 21a measured by sensor 417, outlet pressure 21d measured by sensor 417, and pump rotational speed sensed by RPM sensor 423b, to an approximate flow rate.

The relatively low torque required by motor 411 to squeeze the thin wall tubing according to the present invention allows an additional advantage: it can be set by the user or the manufacturer to limit the maximum pressure that pump 4 generate. This is illustrated with the following example. Pump 4 has a roller diameter of 6" and tube 21, with an ID of ⅜", is used for pumping. To assure that the maximum outlet pressure does not exceed a maximum pressure of 500 mmHg, the maximum torque of the motor (at 0 RPM) would correspond to 3.3 in-lb. If the torque required to squeeze the tubing is 0.7 in-lb (see Table II), then the maximum torque should be 4.0 in-lb. The generated torque of motor 411 can be calculated from the motor speed (sensed by RPM sensor 423a which can be, as known in the art, a tachometer or optical encoder) and the power utilized (sensed by power sensor 423b which can be, as known in the art, the product of the voltage and current applied to the motor winding.) Logic unit 424 can thus calculate the torque, compare it to that set by the user (e.g. 4.0 in-lb), and limit said torque by limiting the power to motor 4 via power controller 432, or set an alarm when the maximum allowed torque is reached. Since the torque increases as the motor is loaded (e.g., increased outlet pressure), control logic unit 424 is designed to either maintain pump speed (i.e. flow) or maintain torque (i.e. outlet pressure). This choice can be made by the user using mode switch 435 on the front panel of display/control unit 425 shown in FIG. 9(d).

The operating range for the inlet 21a and outlet pressure 21d generated by roller pump 4 can also be maintained by varying the power to motor 411 in response to difference between the pressure measured by the aforementioned pressure sensor means and the desired pressure range set by the user. Thus, logic unit 424 monitors said pressure differences, sends control signals to motor 411 via power controller 432 to decrease torque if the said pressure differences become too high.

The thin wall tubing of the present invention not only decreases the torque required to squeeze the tubing, but also allows the use of spring actuated rollers in a heart-lung machine. For example, the spring loaded rollers developed by Cobe Laboratory for dialysis pumps may also be used for high volume applications such as cardiopulmonary bypass. Presently pumps of this type are not used in a heart-lung machine because of hemolysis due to the excess occlusion by the spring loaded rollers and because such occlusion mechanism would require an increase in already large drive motors. However, with the thin wall tubing of the present invention, hemolysis is reduced by reducing the pressure required to occlude the tubing and by providing internal configuration which limits the contacting surface as previously described with respect to FIGS. 7(a) and 7(b). Thus, said pressure members can include at least two rollers which are resiliently biased into engagement with said thin wall tubing with spring 412a incorporated into tubing roller arm 412 of pump 4 and spring 413 incorporated into tubing roller arm 413 as illustrated in FIG. 9(b) and 9(c). Spring 412a pushes tubing roller arm 412 with roller 412b and spring 413a pushes tubing roller arm 413 with roller 413b radially to compress and occlude tube 21 against surface 414a. If thin wall tube 21 has a cross section of the present invention, for example cross section 71 illustrated in FIG. 7(a), then as previously explained with respect to FIGS. 7(a) and 7(b), protrusions 71c and 71d limit the occlusion to a small portion of the wall thereby reducing hemolysis. The fixed channels also provide a uniform and repeatable resistance to backflow. This allows better characterization of the aforementioned equation used to calculate flow from the inlet and outlet pressure and pump speed (RPM).

The force applied by either spring 412a or 413a, shown in FIG. 9(b), required to compress tube 21 to overcome the internal pressure at outlet 21d, can be calculated as the product of the cross sectional area of tube 21 and the pressure at outlet 21d. From the torque analysis described above, and summarized in Table 2, the force required to compress tubing 21 to overcome its elastic wall is relatively low compared to the force required to overcome the outlet pressure. Thus, springs 412a and 412b may be designed to provide sufficient force to overcome the elastic force of the tubing wall and maintain the tubing occluded up to a fixed outlet pressure without introducing a large error due to variation in the elastic force of the tubing. Should the pressure at outlet 21d exceed the force of springs 412a and 413a, rollers 412b and 413b would be pushed back, resulting in a more nonocclusive setting of tubing 21, allowing greater backflow of pumped liquid and thereby limiting outlet pressure.

FIG. 9(b) illustrate a mechanism that allows the user to adjust the resilience bias applied to said rollers and thereby adjust the maximum outlet pressure pump 4 can generate. FIG. 9(c) is a transverse view of pump head 410 taken along lines 4 and 4' as illustrated in FIG. 9(b). The mechanism consists of a conventional occlusion adjuster, 455, as known in the art, (for illustrative purposes the occlusion adjuster design for the Picker International roller pumps will be used) but instead of occlusion adjuster 455 changing the horizontal location of roller arms 412 and 413 directly, it does so via adjusting the compressed length of springs 412a and 413a. Thus, for a higher maximum outlet pressure, the user rotates knob 455a that screws thread 455b into thread 410a advancing plane 455c of occlusion adjuster 455, against plane 453a of slider 453 and plane 454a of slider 454. The vertical motion of occlusion adjuster 455 is transformed into horizontal motion of sliders 453 and 454, said sliders applying greater compression on springs 412a and 413a respectively causing rollers 412b and 413b to push harder against tubing 21. This greater compression will then have to be overcome by a greater pressure in tubing 21 resulting in a higher maximum outlet pressure. Similarly, to lower maximum outlet pressure, the occlusion adjuster would be rotated to reduce the compression of springs 412a and 413a, resulting in a lower compression force upon tubing 21, a lower pressure at outlet 21d required to compress rollers 412 or 413 inward to decrease the aforementioned occlusion and the backflow that limits the maximum pressure at the pump outlet. This adjustment should always be initiated, as known in the art, by setting tube to just complete occlusion and then backing off. All changes thereafter in occlusion adjuster relate to that initial setting.

To assure that the user becomes aware of changes in the degree of occlusion, sensor 453a, incorporated into slider 453, and sensor 454a, incorporated into slider 454, are used to determine the reciprocal position of the rollers. Sensors 453a and 454a can be, for example, force transducers that detect the force that tube 21 exerts on roller 412 or 413 as said rollers squeeze the tubing via springs 412 and 413 respectively. The electric contact between force transducers 453a and 454a and sensor board 423 is made via commutator 458 shown in FIG. 9(d). The reciprocal location of the roller, x, can then be obtained from the measured force, F, and spring constant, K, (e.g. $x = F/K$). The adjustment of maximum pressure can be set by occluding the outlet tubing of pump 4, for example at point 4b of the extracorporeal circuit shown in FIG. 1(a), with a standard tubing clamp, starting pump 4 at a very nonocclusive setting, and slowly increasing the degree of occlusion as the outlet pressure of the pump is monitored until the maximum acceptable pressure is reached. Since during this calibration the outlet of pump 4 is clamped, the backflow must equal the forward flow and therefore the relationship between the degree of occlusion, outlet pressure, pump speed and backflow can also be obtained. This is done by noting the pump speed (RPM), outlet pressure and the signal received from force sensors 456 and 457. Alternatively, this information can be monitored by control logic 424, and the relationship arrived by preset regression analysis equations. Thus when the tubing is clamped, at any pump RPM, or any degree of occlusion and inlet and outlet pressure measured, the net forward flow is zero. During normal operation of the pump, the outlet of pump 4 is not clamped off, and therefore the net flow equals the flow in the tubing when set completely occlusively less the flow corresponding to the RPM that was required to generate the same operating outlet pressure at the same degree of occlusiveness when the pump outlet was clamped off. This can be illustrated with the following example. If under clamped outlet conditions a pump speed of 5 RPM is required to maintain an outlet pressure of 300 mmHg then, with same nonocclusive setting and an outlet pressure of 300 mmHg, the flow generated by the pump at 100 RPM is equivalent to a flow at 95 RPM with the tubing completely occluded.

It should be understood that as the ID of tubing 21 decreases, the spring force should also decrease in proportion to the decreased cross sectional area of the tubing. The adjustment required for different size tubing can be made with the aforementioned occlusion adjuster. Knob 438 of control unit 425, shown in FIG. 9(d), allows the user to select the size of the tubing used to appropriately set the equations used in logic controller 424 for all computations requiring tube size (e.g. flow, maximum pressure).

For any specific set of tubing that maintains the same ID/wall ratio, the ID of the tubing can also be detected by the force sensors 456 and 457. This can be done because with a constant ID/wall, tubing with different size IDs would have a correspondingly different wall thickness. Therefore as the ID increases, the wall thickness increases and the force sensed at any specific aforementioned initial setting of adjusting knob 455 also increases. The increase in force (or its aforementioned derivative x) together with the setting of adjusting knob 455 would dictate the thickness of the wall and therefore the tubing ID.

The characteristics of the thin wall tubing that decrease the torque required to squeeze the tubing also allow precise setting of the roller occlusion. For example, the user can clamp inlet 21a of tube 21, shown in FIG. 8(a), while pump 4 is operating and observe the degree of collapse of tube 21. Since the cross sectional area of thin wall tube 21 is very sensitive to the pressure at inlet 21a, the user by experience with a particular tube could adjust its occlusion, as known in the art, by observing the cross sectional shape that tube 21 takes as the degree of occlusion changes.

Though the above descriptions were for roller pumps used with blood, similar designs can be used for pumping other physiologic solutions, or for industrial roller pumps. For such nonblood applications, it is usually advantageous to have the tubing in an occluded setting. As such, the discussion pertaining to occlusion setting (e.g. the description for cross section 71 shown in FIG. 7(a)) is not applicable. The most applicable cross sections are 31, shown in FIG. 3(a), and 61 shown in FIG. 6(a). In addition, roller pumps with different tube loading (e.g. using stretched silastic over a pump head with three rollers, instead of the two rollers shown in FIG. 9(b)) can also incorporate the design advantages of noninvasive pressure measurements shown in FIG. 9(a), spring loaded rollers that limit outlet pressure as shown in FIGS. 9(b) and 9(c), and the electronic circuitry described in FIG. 9(d). It should also be clear from knowing the art of peristaltic pumps that the aforementioned description for roller pumps can be used to design a low power high efficiency "finger" peristaltic pump wherein said fingers, which replace rollers, are mounted for reciprocation along a plurality of actuating arms.

FIG. 10(a) diagrammatically illustrates control units 15 and clamp 16, previously described with respect to FIG. 1(a), that provide direct control of pressure and flow rate to the patient with a standard roller pump using the monitored pressures from pump inlet 21a and outlet 21d and clamp 16. Control unit 15 incorporates two pressure transducers (not shown) and two digital readouts, 151 and 152, for measuring and indicating inlet 21a and outlet 21d pressures that correspond to points 4a and 4b illustrated in FIG. 1(a) respectively. Unit 15 also incorporates two electronic logic circuits (not shown); one compares the sensed inlet pressure to the maximum value set by the user via controls 153 and the other compares the sensed outlet pressure to the maximum value set by the user via controls 154. The inlet and outlet pressures can be sensed via pressure ports 844 and 854, shown in FIG. 8(a), respectively. The two comparator circuits alarm visually and audibly when either of the measured pressures exceed the set values, and indicate which pressure was exceeded. The control unit may also provide an electric signal to either stop or slow down pump 4. Mode switch 156 allows the user the choice of which pressure combination to use for flow control. Thus, the flow can be controlled by high, low or both high and low pressures extremes, or not at all.

Alternately, control unit 15 can provide an electric signal to activate electrically actuated tube clamp 16. The tubing clamp directs the flow at the outlet of pump 4 to its inlet, thereby limiting the inlet and outlet pressures within set values that are determined by the user. FIG. 10(a) illustrates one type of reciprocating electrically actuated tubing clamp 16 that may be used with control unit 15. As shown, clamp 181 occludes recirculating line 14, also illustrated in FIG. 1(a), and keeps arterial tube 13 open to the patient. When unit 15 activates unit 16, clamp 181 reciprocates to unclamp tube 14 and clamp tube 13 (from first position, point A, to second position, point B). This directs pump 4 output to venous line 11 and stops the flow to the patient via arterial tube 13. The tubing clamp could, for example, be the solenoid operated two tubes pinch valve (model #648P-09 NR Research Inc., Maplewood, N.J.), with the recirculating tube 16, shown in FIG. 1(a), normally closed and the other tube normally open. It could also be a unit similar to that made by Gambro (Newport News, Va.) for single needle dialysis (Model #SN10). The other tube could be either venous line 11 or arterial line 13. It should be understood that the degree of clamping need not be complete but could be done in steps to allow partial occlusion of recirculating line 14. For example the degree of recirculation through line 14 can be controlled by using a proportional solenoid with a stroke that is proportional to the input current (e.g. similar to PS16 made by Lucas Ledex of Vandaila, Ohio). The input current can be controlled by the difference between the maximum set pressure and the pressure measured from inlet and outlet pressure as determined by the comparator described for control unit 15. A much finer control over the travel of the clamp, and therefore the degree by which the clamp occludes the recirculation tubing 14, can be achieved with a stepper motor driving a tubing clamp whose occlusion is adjusted by rotation. This can be achieved in a manner similar to that used for controlled intravenous (IV) gravity infusion pumps as made by Kendall McGaw (MetriPro model) or similar models made by Abbott or Baxter/Travenol.

Alternately, the degree of recirculation can be controlled by intermittently actuating the solenoid to unclamp the recirculating tube with the timing circuit illustrated in FIG. 10(b). The proportion of the unclamp time to clamp time can be controlled with two electronic timers, 111 and 112, (e.g. 556 dual timer by National Semiconductor) with first timer 111 triggering second timer 112. First timer 111 controls the interval between the cycles, or the frequency of clamping. Second timer 112 controls the time that power is applied to the solenoid clamp. The ON time produced by timer 112 is electronically amplified to either drive solenoid actuated clamp 16 directly or via relay 113. Relay 113 is preferably a solid state relay. The function of the intermittent clamping is hereby illustrated by an example. If first timer 111 is set to trigger second timer 112 every 4 seconds and second timer is set for 2 seconds, then the solenoid would unclamp the tubing for 2 sec every 4 sec. This would give a 50% unclamp time, or the flow to the patient would be about 50% of the pump flow. To automate the system, first timer 111 could be fixed and the ON time of second timer could be controlled by the difference between the maximum set pressure and the pressure measured from inlet and outlet pressure as determined by the comparator described for control unit 15. This logic, known as negative feedback, would be used to assure that as the measured pressures approaches the set pressures, the unclamp time increases. The increased unclamp time would reduce outlet pressure and increase inlet pressure, either one of which would reduce feedback signal and therefore the unclamp time.

With any of the aforementioned controls that provides recirculation of the outlet blood, flow is provided to the patient, even if it is lower than the flow provided by pump 4. Thus control unit 15 and clamp 16, when used with present innovative tubing provide recirculation that allows standard roller pumps to be controlled by inlet and outlet pressure as presently provided only by expensive computer controlled pumps. It should be understood that the recirculation mechanism can also be used, though not as effectively, in a circuit using standard tubing and means to measure inlet and outlet pressures.

It should be understood that the same relationship that presently exists between roller pumps and linear peristaltic pumps can be developed between the roller pump described in FIGS. 9(a), 9(b), 9(c), and 9(c). Thus, all the advantages realized with a roller pump utilizing the present innovative thin wall tubing, can also be realized with parallel design for IV infusion pumps as described in reference to FIG. 1(b). Likewise, it should be understood that comprehensive descriptions of all the applications of the inventions is beyond the scope of a patent application and therefore the aforementioned descriptions are given as illustrations and should not be used to limit the intent, spirit, or scope of the invention.

What is claimed is:

1. The combination of an extruded thin wall tubing and a peristaltic pump having at least two rollers, said tubing having an unreinforced outer wall which is directly engaged by said rollers and a low spallative wall resistant to fatigue spalling, said tubing extruded of an elastomeric thermoplastic material formed with a predetermined set curvature having an inner diameter to thin wall thickness ratio of at least 9 to 1, said tubing having a substantially improved pumping lifetime and the ability to withstand an outlet pressure of at least 300 mmHg.

2. The combination of an extruded thermoplastic tubing and a peristaltic pump, said tubing having an offset inner diameter which forms an eccentric tubing with a thin wall portion, said tubing having a pair of fittings which orient the tubing to be mounted in said pump such that the sum of the thickness of opposite walls is constant when compressed by said peristaltic pump, said tubing having a ratio of inner diameter to thickness of said thin wall portion of at least 9 to 1, an inner wall resistant to fatigue spalling and a substantially improved pumping lifetime.

3. A method of using the combination of an extruded polyurethane tubing and a peristaltic pump, said method including compressing said tubing with at least two rollers which directly engage a nonreinforced outer wall of said tubing, said tubing formed with a thin wall portion, with a ratio of inner diameter to thickness of said thin wall portion of at least 9 to 1, a wall resistant to fatigue spalling, said method providing a substantially improved pumping lifetime, with said thin wall portion providing substantially improved pump efficiency.

4. The combination of an extruded polyether-polyurethane tubing and a peristaltic roller pump, said pump having at least two rollers for directly engaging an unreinforced outer wall of said tubing, said tubing having a thin wall portion and a predetermined set curvature with an inner diameter to wall thickness ratio of at least 9 to 1, an inner diameter 0.625 inch or less, and a shore hardness of, at least 60 A, said tubing having a flow sensitivity to inlet pressure equal to $K(ID/wall)^3$ wherein K is a constant that decreases with increased wall durometer, said flow sensitivity providing a decrease in flow of at least 25% for a drop in inlet pressure of 100 mmHg below 0 mmHg, said tubing having an inner wall resistant to fatigue spalling with a substantially improved pumping lifetime.

5. The combination of an extruded polyether-polyurethane thin wall tubing for use in pumping blood and a peristaltic pump, said tubing having an inner diameter to thin wall thickness ratio of at least 9 to 1, said tubing having at least first and second inner longitudinal ribs formed therein, to define a non-occlusive blood passageway therebetween which minimizes wall contact and hemolysis when said tubing is collapsed by said peristaltic pump.

6. An improved thin wall tubing as claimed in claim 5, wherein said ribs extend inwardly from 0.010 to 0.050 inches.

7. A method for manufacturing an thin wall pumping tube for use in a peristaltic pump having a raceway, said method comprising:
   (a) extruding a tube from a polymeric elastomer with a thin wall portion having an inner diameter to thin wall thickness ratio of at least 9 to 1, said tubing having a low spallative wall resistant to fatigue spalling and the ability to withstand an outlet pressure of at least 300 mmHg;
   (b) setting a predetermined curvature on said tubing after said extrusion step while said tubing is cooled;
   (c) setting said curvature to assure that when said tubing is placed in a peristaltic pump, said thin wall portion will be compressed to form a line parallel to said pump raceway and perpendicular to an axis of occlusion;
   (d) whereby said improved thin wall tubing has a substantially increased pump lifetime.

8. A low power, high efficiency peristaltic pump, said pump comprising:
   (a) a thin wall extruded tubing with the thin wall having an inner diameter to thin wall thickness ratio of at least 9 to 1, said tubing having an inlet and an outlet and formed with a predetermined set curvature;
   (b) a first means to directly engage said thin wall tubing for non-invasively measuring the pressure of a fluid within said thin wall tubing at said inlet and said outlet, and generating pressure signals in response thereto;
   (c) a second means for directly engaging the outer wall of said tubing and sequentially occluding said thin wall tubing to pump a fluid therethrough.
   (d) the combination providing a high pumping efficiency wherein at 250 mmHg outlet pressure, no more than 35% of the power consumed by the pump is used in compressing said thin wall tubing.

9. A low power high efficiency pump for extra-corporeal circulation, said pump comprising:
   (a) a thin wall extruded tubing with the thin wall having an inner diameter to thin wall thickness ratio of at least 9 to 1, said tubing having an inlet and an outlet and formed with a predetermined set curvature;
   (b) at least a pair of rotating and resiliently biased rollers for directly engaging the outer wall of said tubing and sequentially and at least partially occluding the thin wall tubing to pump blood therethrough;
   (c) a direct drive motor for rotating said rollers to at least partially occlude said thin wall tubing;
   (d) the combination providing a high pumping efficiency wherein at 250 mmHg outlet pressure, no more than 35% of the power consumed by the pump is used in compressing said thin wall tubing.

10. A method for using an extruded polyether-polyurethane tubing in a peristaltic pump, said method including compressing said tubing with a plurality of tube engaging elements which directly engage a nonreinforced outer wall of said tubing, said tubing formed with a thin wall portion, with a ratio of inner diameter to thickness of said thin wall portion of at least 9 to 1, an inner wall resistant to fatigue spalling, said method providing a substantially improved pumping lifetime with said thin wall portion providing substantially improved pump efficiency.

11. An extruded polyurethane tubing for use in pumping blood in a peristaltic roller pump, said pump having at least two rollers for directly engaging an unreinforced outer wall of said tubing, said tubing having a thin wall portion with an inner diameter to wall thickness ratio of at least 9 to 1 and formed with a predetermined set curvature, an inner diameter of 0.625 inch or less, and a shore hardness of at least 60 A, said tubing having a flow sensitivity to inlet pressure equal to $K(ID/wall)^3$ wherein K is a constant that decreases with increased wall durometer, said flow sensitivity providing a decrease in flow of at least 25% for a drop in inlet pressure of 100 mmHg, below 0 mmHg, said tubing having an inner wall resistant to fatigue spalling with a substantially improved pumping lifetime.

12. An extruded thermoplastic thin wall tubing for using in pumping blood in peristaltic pumps, said tubing having an inner diameter to thin wall thickness ratio of at least 9 to 1 and formed with a predetermined set curvature, said tubing having at least first and second inner longitudinal ribs formed therein, to define a non-occlusive blood passageway therebetween which minimizes wall contact and hemolysis when said tubing is collapsed by said peristaltic pump.

13. A combination of an extruded tubing having a thin wall and an extracorporeal circuit for surgery or dialysis, wherein said improved extruded tubing is particularly adapted for use in a peristaltic pump, said tubing having an unreinforced outer wall which is directly engaged by said peristaltic pump, and a low spallative wall resistant to fatigue spalling, said tubing extruded from a polymeric thermoplastic elastomer to form a tube having an inner diameter to thin wall thickness ratio of at least 9 to 1 and formed with a predetermined set curvature, said tube having a substantially improved pumping lifetime and the ability to withstand and outlet pressure of at least 300 mmHg.

14. The combination of an extruded tubing having a thin wall and a peristaltic pump having a plurality of tube engaging elements, said tubing having an unreinforced outer wall which is directly engaged by said tube engaging elements and a low spallative wall resistant to fatigue spalling, said tubing extruded of a polymeric thermoplastic elastomer having an inner diameter to thin wall thickness ratio of at least 9 to 1 and formed with a predetermined set curvature, said tubing having a substantially improved pumping lifetime and the ability to withstand and outlet pressure of at least 300 mmHg.

15. An improved thin wall tubing as claimed in claim 2 or 3 wherein said tubing has a uniform internal lumen with said thin wall portion extending at least 185° but not more than 355° of its circumference to promote the formation of bleed channels when used in a peristaltic pump.

16. An improved thin wall tubing as claimed in claim 2 or 3 wherein said tubing has a uniform external circumference and said thin wall portion extending at least 185° but not more than 355° of its circumference to promote the formation of bleed channels when in used in a peristaltic pump.

17. The combination of an extruded thin wall tubing and a peristaltic pump, as claimed in claim 1 or 2 or 4 or 13 or 14 wherein said tubing further includes at least one fitting which encloses a portion of said thin wall tubing and a transducer means to non-invasively measure fluid pressure through the wall of said tubing.

18. The combination of an thin wall tubing and a peristaltic pump as claimed in claim 17 wherein said transducer further includes means to engage the outer wall of the tubing to non-invasively obtain a measurement of fluid pressure within said tubing.

19. The combination of a thin wall tubing and a peristaltic pump, as claimed in claimed in claim 1 or 2 or 4 or 13 or 14 wherein said tubing has a first and a second longitudinal rib formed therein.

20. An improved thin wall tubing as claimed in claim 6, wherein said ribs extend outwardly from 0.010 to 0.050 inches.

21. An improved thin wall tubing as claimed in claim 1 or 2 or 6, or 16 wherein said tubing is formed of polyether-polyurethane.

22. An thin wall tubing for use in peristaltic pumps as claimed in Claim 1 or 2 or 4 or 13 or 14 wherein said pump further includes means to engage the outer wall of the tubing to non-invasively obtain a measurement of fluid pressure within said tubing.

23. A low power, high efficiency peristaltic I.V. pump for physiological fluid, said pump comprising:
 (a) a thin wall extruded thermoplastic tubing with the thin wall having an inner diameter of less than 0.25 inches and an inner diameter to thin wall thickness ratio of at least 9 to 1, said tubing having inlet and an outlet;
 (b) a first means to directly engage said thin wall tubing for non-invasively measuring the pressure of a physiological fluid within said thin wall tubing at said inlet and said outlet, and generating pressure signals in response thereto;
 (c) a second means for directly engaging the outer wall of said tubing and sequentially occluding said thin wall tubing to pump a fluid therethrough;
 (d) the combination providing a high pumping efficiency wherein at 250 mmHg outlet pressure, no more than 35% of the power consumed by the pump is used in compressing said thin wall tubing.

24. A low power, high efficiency peristaltic I.V. pump for physiological fluids, said pump comprising:
 (a) a thin wall extruded thermoplastic tubing having an offset inner diameter which forms an eccentric tubing with a thin wall having an inner diameter to thin wall thickness ratio of at least 9 to 1, said tubing having an inlet and an outlet, said tubing having means to orient the tubing in said pump such that the sum of the thickness of opposite walls is constant when compressed by said peristaltic pump;
 (b) a first means to directly engage said thin wall tubing for non-invasively measuring the pressure of a physiological fluid within said thin wall tubing at said inlet and said outlet, and generating pressure signals in response thereto;
 (c) a second means for directly engaging the outer wall of said tubing and sequentially occluding said thin wall tubing to pump a fluid therethrough;
 (d) the combination providing a high pumping efficiency wherein at 250 mmHg pressure, no more than 35% of the power consumed by the pump is used in compressing said thin wall tubing.

25. The combination of an extruded polyurethane tubing and a peristaltic roller pump, said pump having at least two rollers for directly engaging an unreinforced outer wall of said tubing, said tubing having an offset inner diameter which forms an eccentric tubing and a thin portion with an inner diameter to wall thickness ratio of at least 9 to 1, said tubing including means to orient the tubing in said pump such that the sum of the thickness of opposite walls is constant when compressed by said peristaltic pump, said tubing having an inner diameter of 0.625 inches or less, and a shore hardness of at least 60 A, said tubing having a flow sensitivity to inlet pressure equal to $K (ID/wall)^3$ wherein K is a constant that decreases with increased wall durometer, said flow sensitivity providing a decrease in flow of at least 25% for a drop in inlet pressure of 100 mmHg to below 0 mmHg, said tubing having an inner wall resistant to fatigue spalling with a substantially improved pumping lifetime.

* * * * *